(12) United States Patent
Park et al.

(10) Patent No.: US 10,676,425 B2
(45) Date of Patent: Jun. 9, 2020

(54) ALPHA-AMINOAMIDE DERIVATIVE COMPOUND AND PHARMACEUTICAL COMPOSITION COMPRISING SAME

(71) Applicant: Megabiowood Co., Ltd., Hwasun-gun (KR)

(72) Inventors: Ki Duk Park, Seoul (KR); ChangJoon Justin Lee, Seoul (KR); Dong Jin Kim, Seoul (KR); Ae Nim Pae, Seoul (KR); Hyun Ah Choo, Seoul (KR); Sun Joon Min, Seoul (KR); Yong Koo Kang, Seoul (KR); Yun Kyung Kim, Seoul (KR); Hyo Jung Song, Seoul (KR); Ji Won Choi, Seoul (KR); Min Ho Nam, Seoul (KR); Jun Young Heo, Seoul (KR); Seul Ki Yeon, Seoul (KR); Bo Ko Jang, Seoul (KR); Eun Ji Ju, Seoul (KR); Seon Mi Jo, Seoul (KR); Jong-Hyun Park, Seoul (KR)

(73) Assignee: MEGABIOWOOD CO., LTD, Hwasun-Gun (KR)

( * ) Notice: Subject to any disclaimer, the term of this patent is extended or adjusted under 35 U.S.C. 154(b) by 0 days.

(21) Appl. No.: 15/516,395

(22) PCT Filed: Sep. 24, 2015

(86) PCT No.: PCT/KR2015/010104
§ 371 (c)(1),
(2) Date: Apr. 1, 2017

(87) PCT Pub. No.: WO2016/052928
PCT Pub. Date: Apr. 7, 2016

(65) Prior Publication Data
US 2017/0298011 A1 Oct. 19, 2017

(30) Foreign Application Priority Data

Oct. 2, 2014 (KR) .................. 10-2014-0132983
Sep. 18, 2015 (KR) .................. 10-2015-0132281

(51) Int. Cl.
| | | |
|---|---|---|
| C07C 237/06 | (2006.01) |
| C07C 231/12 | (2006.01) |
| C07C 237/04 | (2006.01) |
| C07C 237/20 | (2006.01) |
| A61K 31/167 | (2006.01) |
| C07C 309/04 | (2006.01) |
| A61K 31/16 | (2006.01) |

(52) U.S. Cl.
CPC ............ *C07C 237/06* (2013.01); *A61K 31/16* (2013.01); *A61K 31/167* (2013.01); *C07C 231/12* (2013.01); *C07C 237/04* (2013.01); *C07C 237/20* (2013.01); *C07C 309/04* (2013.01)

(58) Field of Classification Search
CPC combination set(s) only.
See application file for complete search history.

(56) References Cited

U.S. PATENT DOCUMENTS

| 5,391,577 A | 2/1995 | Dostert et al. |
| 8,283,380 B2 | 10/2012 | Fariello et al. |

FOREIGN PATENT DOCUMENTS

| CN | 102274517 A | 12/2011 |
| KR | 10-2016-0039817 A | 4/2016 |
| RU | 2397160 C9 | 8/2010 |
| WO | 2004089353 A2 | 10/2004 |
| WO | 2012078994 A1 | 6/2012 |

OTHER PUBLICATIONS

Antonio Arcadi et al., A Mild and Versatile Method for Palladium-Catalyzed Cross-Coupling of Aryl Halides in Water and Surfactants, Eur. J. Org. Chem., Jun. 12, 2003, pp. 4080-4086.
Linh Vong et al., Leptin Action on GABAergic Neurons Prevents Obesity and Reduces Inhibitory Tone to POMC Neurons, Neuron, Jul. 13, 2011, pp. 142-154, vol. 71.
Hirokazu Yano, Nickel-Catalyzed Suzuki Coupling Reactions of Aryl Chlorides with Arylbornnic Acids, TOSOH Research & Technology Rev, Dec. 31, 2009, pp. 33-39, vol. 53.
Pevarello et al. Synthesis and Anticonvulsant Activity of a New Class of 2-[(Arylalkyl)amino]alkanamide Derivatives, Journal of Medicinal Chemistry, Jan. 28, 1998, pp. 579-590 , vol. 41, No. 4.
Dinesh Dhingra et al. Inhibition of MAO and GABA: Probable mechanisms for antidepressant-like activity of Nardostachys jatamansi DC. in mice, Indian Journal of Experimental Biology, Apr. 2008,pp. 212-218, vol. 46.
Francesco Leonetti et al., Solid-Phase Synthesis and Insights into Structure-Activity Relationships of Safinamide Analogues as Potent and Selective Inhibitors of Type B Monoamine Oxidase, Journal of Medicinal Chemistry, Sep. 7, 2007,pp. 4909-4916, vol. 50, No. 20.
Seonmi Jo et al., GABA from reactive astrocytes impairs memory in mouse models of Alzheimer's disease, Nature Medicine, Jun. 29, 2014, pp. 1-15, Advance Online Publication.
Kyung Joon Min,Other Uses of Bupropion, Department of Psychiatry, Korean J Psychopharmacol , 2005, pp. 25-32, vol. 16(1):College of Medicine, Chung-Ang University, Seoul, Korea.

*Primary Examiner* — Ana Z Muresan
(74) *Attorney, Agent, or Firm* — Goldilocks Zone IP Law

(57) ABSTRACT

The present disclosure relates to an α-aminoamide derivative compound and a pharmaceutical composition containing the same, for treating a neurodegenerative diseases.

2 Claims, 12 Drawing Sheets

Safinamide (SP score: −10.862 kcal/mol)

Compound 9 (SP score: −11.795 kcal/mol)

ALPHA-AMINOAMIDE DERIVATIVE COMPOUND AND PHARMACEUTICAL COMPOSITION COMPRISING SAME

CROSS REFERENCE TO RELATED PATENT APPLICATIONS

This application claims the benefit under 35 U.S.C. Section 371, of PCT International Application No. PCT/KR2015/010104, filed Sep. 24, 2015, which claimed priority to Korean Patent Application No. 10-2014-0132983 filed Oct. 2, 2014 and Application No.: 10-2015-0132281 filed Sep. 18, 2015, the disclosures of which are hereby incorporated by the references.

TECHNICAL FIELD

The present disclosure relates to an α-aminoamide derivative compound and a pharmaceutical composition containing the same.

BACKGROUND ART

Parkinson's disease is a progressive disease which is the second most common neurodegenerative disease. It is estimated that there are about 6.3 million Parkinson's disease patients globally, with about 1 out of 1,000 people. Although Parkinson's disease occurs common in the elderly, it occurs in young people too. Parkinson's disease is not easily distinguished from other diseases because the symptoms develop slowly. It is not easily detected in early stages and is accompanied by abnormal clinical symptoms such as tremor, stiffness, slowing of movement, postural instability, stooped posture, freezing of gait, depression, sleep disorder, dysuria, dementia, etc.

Although the cause of Parkinson's disease is not clear, it is known to be caused by deficiency in dopamine resulting from the loss of neurons that secrete the neurotransmitter dopamine in the brain. At present, the levodopa therapy of administering levodopa which is converted into dopamine in the body is commonly used. Although levodopa is the most effective therapeutic agent for Parkinson's disease, decreased drug efficacy or various motor disorders can occur during treatment. As alternative medications, COMT inhibitors, MAO-B inhibitors, etc., which maintain the concentration of dopamine in the brain by inhibiting the metabolism of dopamine, are used.

It is known that MAO-B not only plays an important role in dopamine metabolism in the brain but also inhibits damage to cranial nerve cells. Although there is no clear evidence that the MAO-B inhibitor actually delays the progress of Parkinson's disease, it is known that inhibition of MAO-B leads to inhibition of denaturation or destruction of dopaminergic neurons because it plays an important role in the onset of Parkinson's disease by MPTP or similar environmental toxicants. Also, there are evidences from animal and clinical tests that the MAO-B inhibitor has an effect of protecting the brain unlike other drugs.

Selegiline, which is approved as the most representative MAO-B inhibitor, is prescribed as a therapeutic agent for Parkinson's disease. However, it causes hepatotoxicity because it is metabolized to amphetamine and the irreversible inhibitor is accompanied by various side effects. Since rasagiline (Azilect) was first marketed in 2005 in Israel, it was marketed in about 50 countries including Europe, USA, etc. Azilect is free from amphetamine side effects and exhibits better efficacy than other dopaminergic drugs. However, although rasagiline also exhibits superior effect of inhibiting MAO-B like selegiline as an irreversible MAO-B inhibitor, it has a safety problem. Therefore, drugs that can effectively and reversibly inhibit the activity of MAO-B while solving the above-described disadvantages are being developed. However, no noticeable reversible inhibitor is available yet.

Obesity refers to a medical condition in which excess body fat has accumulated to the extent that it may have a negative effect on health. It is a condition in which excess energy has accumulated due to the difference in energy intake and energy expenditure. Obesity increases the likelihood of various diseases.

Because the previous studies on the hypothalamus regarding the regulation of food intake have been conducted centered on neurons as part of the brain, the understanding of the diet/obesity regulation by the brain has been limited. Therefore, study on glial cells (glia) which account for a greater part is necessary for a comprehensive understanding of the brain function. Recently, astrocytes which are the most abundant of the glial cells are spotlighted as cells that can activate or suppress nearby neurons by secreting various signaling molecules such as GABA (gamma-aminobutyric acid), glutamate, D-serine, ATP, etc. Astrocytes of the hypothalamus, which closely interact with POMC (pro-opiomelanocortin) neurons and express leptin receptors, can also contribute to leptin signaling.

In the hypothalamus, there exist two groups of POMC neurons, one that stimulates appetite and the other that stimulates energy consumption. Under normal situations, the astrocytes help the activation of nearby POMC neurons which stimulate energy consumption. However, in obesity, they turn to reactive astrocytes due to excessive leptin signals and putrescine is turned to GABA and secreted by MAO-B (monoamine oxidase B). In addition, the POMC neurons that stimulate energy consumption express GABAa receptors outside synapses including the a4, a5 and a6 subunits due to excessive leptin signals and are affected by the GABA secreted by the reactive astrocytes. As a result, the POMC neurons are inhibited and energy consumption is decreased, leading to accumulation of fats.

If MAO-B, which is the enzyme responsible for production of GABA, is inhibited, the production and secretion of GABA are inhibited and energy consumption is promoted as the POMC neurons are activated again. However, the POMC neurons that suppress appetite are not affected by GABA because they do not express GABAa receptors outside synapses. Therefore, the MAO-B inhibitors act on the POMC neurons which selectively excite energy consumption, thereby exhibiting an effect of treating obesity. However, most of the existing MAO-B inhibitors exhibit various side effects as irreversible inhibitors. Although drugs that can reversibly inhibit MAO-B are studied and developed for this reason, no noticeable reversible MAO-B inhibitor that can effectively act on obesity is available yet.

DISCLOSURE

Technical Problem

The present disclosure is directed to overcoming the disadvantages of existing drugs used as MAO-B inhibitors. It is directed to developing a therapeutic agent that reversibly inhibits MAO-B through a non-covalent bond so as to alleviate or eliminate the side effects of the existing drugs which exhibit a therapeutic effect by irreversibly acting via a covalent bond with MAO-B. It is also directed to providing a compound which has superior stability and efficacy compared to the existing reversible MAO-B inhibitors, a composition containing the same and a method for preparing the same.

Technical Solution

In an aspect, the present disclosure provides an α-aminoamide derivative represented by Chemical Formula 1 or a pharmaceutically acceptable salt thereof.

[Chemical Formula 1]

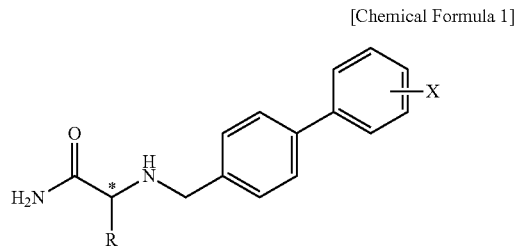

wherein R and X are defined in the detailed description.

In another aspect, the present disclosure relates to a monoamine oxidase B (MAO-B) inhibitor containing the α-aminoamide derivative according to various exemplary embodiments of the present disclosure or a pharmaceutically acceptable salt or solvate thereof as an active ingredient.

In another aspect, the present disclosure relates to a pharmaceutical composition for treating or preventing a neurodegenerative disease, which contains the α-aminoamide derivative according to various exemplary embodiments of the present disclosure or a pharmaceutically acceptable salt or solvate thereof as an active ingredient.

In another aspect, the present disclosure relates to a use of the α-aminoamide derivative according to various exemplary embodiments of the present disclosure or a pharmaceutically acceptable salt or solvate thereof for preparation of a drug for treating or preventing a neurodegenerative disease.

In another aspect, the present disclosure relates to a method for treating or preventing a neurodegenerative disease by administering a pharmaceutical composition containing the α-aminoamide derivative according to various exemplary embodiments of the present disclosure or a pharmaceutically acceptable salt or solvate thereof to a mammal.

In another aspect, the present disclosure relates to a pharmaceutical composition for treating or preventing obesity, which contains the α-aminoamide derivative according to various exemplary embodiments of the present disclosure or a pharmaceutically acceptable salt or solvate as an active ingredient.

In another aspect, the present disclosure relates to a method for preparing the α-aminoamide derivative represented by Chemical Formula 1.

Advantageous Effects

According to various exemplary embodiments of the present disclosure, provided is a therapeutic agent which can overcome the disadvantages of existing drugs used as a MAO-B inhibitor and, specifically, reversibly inhibits MAO-B through a non-covalent bond so as to alleviate or eliminate the side effects of the existing drugs which exhibit a therapeutic effect by irreversibly acting via a covalent bond with MAO-B. Particularly, a new compound having superior stability and efficacy compared to the existing reversible MAO-B inhibitors may be provided.

BEST MODE

Figure 1:
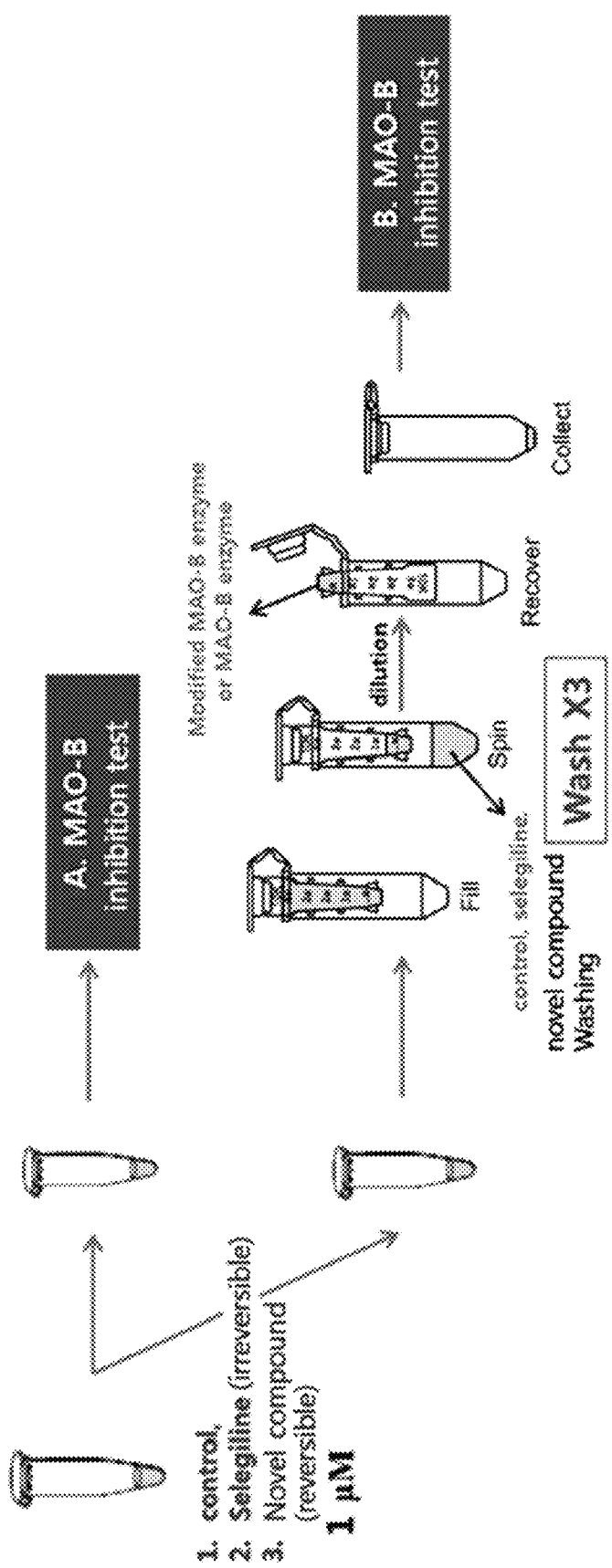
FIG. 1 shows a procedure for testing the reversibility of an α-aminoamide derivative according to an exemplary embodiment of the present disclosure for MAO-B (monoamine oxidase B).

Hereinafter, several aspects and various exemplary embodiments of the present disclosure are described in more detail.

The present disclosure relates to an α-aminoamide derivative represented by [Chemical Formula 1] or a pharmaceutically acceptable salt thereof:

[Chemical Formula 1]

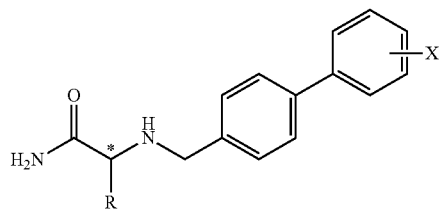

wherein R is hydrogen or $C_{1-7}$ alkyl; and X is selected from a halogen, alkyl, halogenated alkyl, alkoxy and halogenated alkoxy.

The asterisk (*) denotes optical activity.

In an exemplary embodiment, R is selected from hydrogen and $C_1$-$C_7$ alkyl; and X is selected from a halogen, $C_1$-$C_7$ alkyl, halogenated $C_1$-$C_7$ alkyl, $C_1$-$C_7$ alkoxy and halogenated $C_1$-$C_7$ alkoxy.

In another exemplary embodiment, R is selected from hydrogen, methyl, ethyl, n-propyl, isopropyl, cyclopropyl, n-butyl, isobutyl, sec-butyl and tert-butyl; and X is selected from a halogen, halogenated methyl, halogenated ethyl, halogenated methoxy, halogenated ethoxy, methoxy and ethoxy. In particular, in this case, the effect of relieving antibody-dependent cellular cytotoxicity can be achieved additionally.

In another exemplary embodiment, R is selected from hydrogen, methyl, isopropyl and isobutyl; and X is selected from fluoro, chloro, trifluoromethyl, trifluoromethoxy and methoxy. In particular, in this case, channel inhibitory effect is almost absent and is remarkably lower than that of safinamide which is well known as a MAO-B inhibitor. Accordingly, stability as a selective MAO-B inhibitor can be ensured.

In another exemplary embodiment, R is selected from hydrogen, methyl, isopropyl and isobutyl; and X is selected from p-trifluoromethyl, p-trifluoromethoxy, m-trifluoromethyl, m-trifluoromethoxy, p-chloro, m-chloro, p-methoxy, m-methoxy, p-fluoro and m-fluoro.

In another exemplary embodiment, R is selected from hydrogen, methyl, isopropyl and isobutyl; and X is selected from p-trifluororomethyl, p-trifluoromethoxy, m-trifluoromethyl,
m-trifluoromethoxy, p-chloro, m-chloro, p-methoxy and m-methoxy. In another exemplary embodiment, R is hydrogen or methyl; and X is selected from p-trifluoromethyl, p-trifluoromethoxy, m-trifluoromethyl, m-trifluoromethoxy, p-chloro, m-chloro, p-methoxy and m-methoxy.

In another exemplary embodiment, R is hydrogen or methyl; and X is selected from p-trifluoromethyl, p-trifluoromethoxy, m-trifluoromethyl and m-trifluoromethoxy. In particular, in this case, the effect of completely blocking antibody-dependent cellular cytotoxicity can be achieved additionally.

In another exemplary embodiment, R is hydrogen or methyl; and X is p-trifluoromethyl or p-trifluoromethoxy.

In another exemplary embodiment, R is methyl; and X is p-trifluoromethyl or p-trifluoromethoxy.

In another exemplary embodiment, R is methyl; and X is p-trifluoromethyl.

In another exemplary embodiment, the α-aminoamide derivative is selected from the following compounds:
(S)-2-(((2'-fluorobiphenyl-4-yl)methyl)amino)propanamide methanesulfonate,
(S)-2-(((3'-fluorobiphenyl-4-yl)methyl)amino)propanamide methanesulfonate,
(S)-2-(((4'-fluorobiphenyl-4-yl)methyl)amino)propanamide methanesulfonate,
(S)-2-(((2'-chlorobiphenyl-4-yl)methyl)amino)propanamide methanesulfonate,
(S)-2-(((3'-chlorobiphenyl-4-yl)methyl)amino)propanamide methanesulfonate,
(S)-2-(((4'-chlorobiphenyl-4-yl)methyl)amino)propanamide methanesulfonate,
(S)-2-(((2'-trifluoromethylbiphenyl-4-yl)methyl)amino)propanamide methanesulfonate,
(S)-2-(((3'-trifluoromethylbiphenyl-4-yl)methyl)amino)propanamide methanesulfonate,
(S)-2-(((4'-trifluoromethylbiphenyl-4-yl)methyl)amino)propanamide methanesulfonate,
(S)-2-(((3'-trifluoromethoxybiphenyl-4-yl)methyl)amino)propanamide methanesulfonate,
(S)-2-(((4'-trifluoromethoxybiphenyl-4-yl)methyl)amino)propanamide methanesulfonate,
(S)-2-(((3'-methoxybiphenyl-4-yl)methyl)amino)propanamide methanesulfonate,
(S)-2-(((4'-methoxybiphenyl-4-yl)methyl)amino)propanamide methanesulfonate,
(R)-2-(((3'-fluoromethoxybiphenyl-4-yl)methyl)amino)propanamide methanesulfonate,
(R)-2-(((4'-trifluoromethylbiphenyl-4-yl)methyl)amino)propanamide methanesulfonate,
(R)-2-(((4'-trifluoromethylbiphenyl-4-yl)methyl)amino)acetamide methanesulfonate,
(R)-3-methyl-2-(((4'-trifluoromethylbiphenyl-4-yl)methyl)amino)butanamide methanesulfonate and
(R)-4-methyl-2-(((4'-trifluoromethylbiphenyl-4-yl)methyl)amino)pentanamide methanesulfonate.

In another exemplary embodiment of the present disclosure, the α-aminoamide derivative according to various exemplary embodiments of the present disclosure may be an (S)-isomer.

In the present disclosure, the pharmaceutically acceptable salt includes an inorganic acid salt such as hydrochloride, hydrobromide, phosphate or sulfate and an organic acid salt such as carboxylate or sulfonate, although not being limited thereto. The carboxylate includes acetate, maleate, fumarate, malate, citrate, tartrate, lactate or benzoate, although not being limited thereto. The sulfonate includes methanesulfonate, ethanesulfonate, benzenesulfonate, toluenesulfonate or naphthalenedisulfonate, although not being limited thereto.

The present disclosure also provides a method for preparing an α-aminoamide derivative, which includes:

(A) a step of synthesizing a compound of [Chemical Formula 1c] by reacting a compound of [Chemical Formula 1a] with a compound of [Chemical Formula 1b]:

[Chemical Formula 1a]
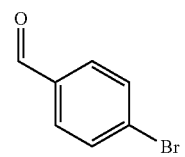

[Chemical Formula 1b]
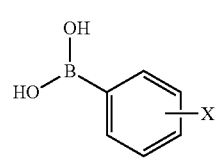

[Chemical Formula 1c]
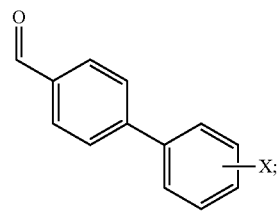

(B) a step of synthesizing a compound of [Chemical Formula 1e] by reacting the compound of [Chemical Formula 1c] with a compound of [Chemical Formula 1d]:

[Chemical Formula 1d]

[Chemical Formula 1e]

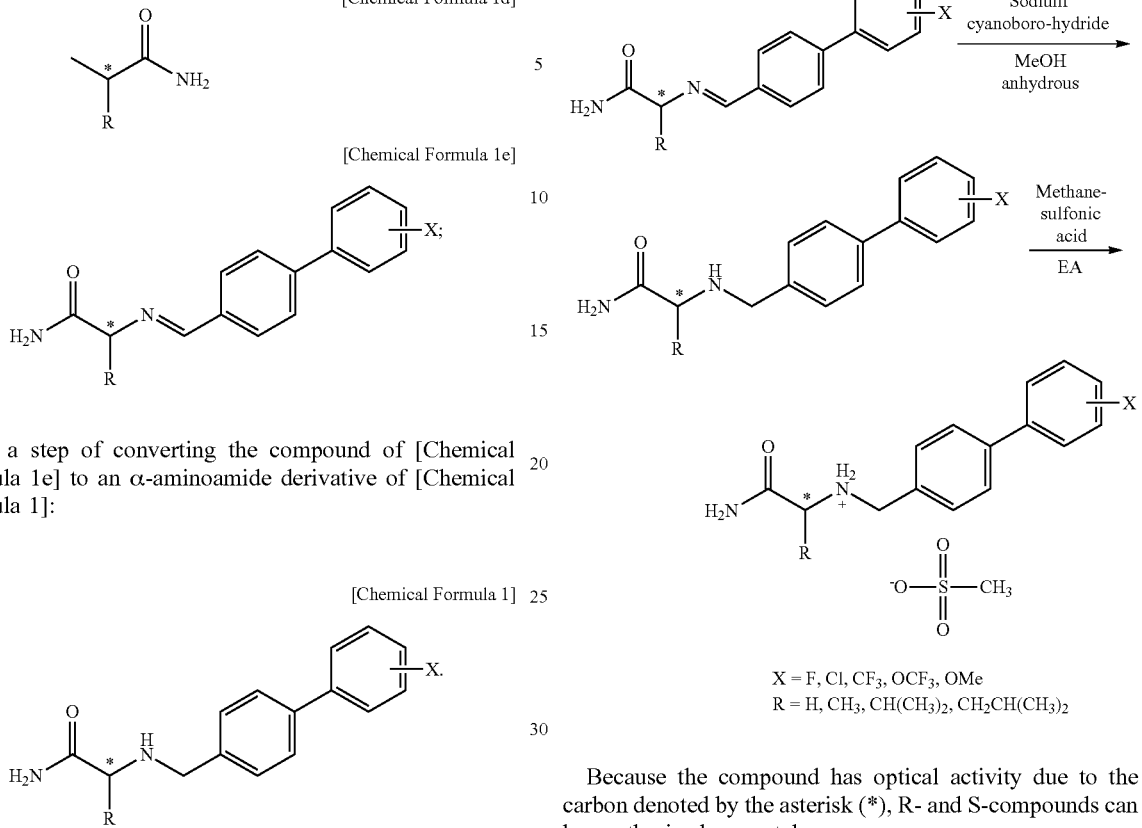

X = F, Cl, CF$_3$, OCF$_3$, OMe
R = H, CH$_3$, CH(CH$_3$)$_2$, CH$_2$CH(CH$_3$)$_2$ (C) a step of converting the compound of [Chemical Formula 1e] to an α-aminoamide derivative of [Chemical Formula 1]:

[Chemical Formula 1]

In [Chemical Formula 1] and [Chemical Formula 1b] through [Chemical Formula 1e], R and X are the same as defined above.

The preparation method may be expressed by [Scheme 1]:

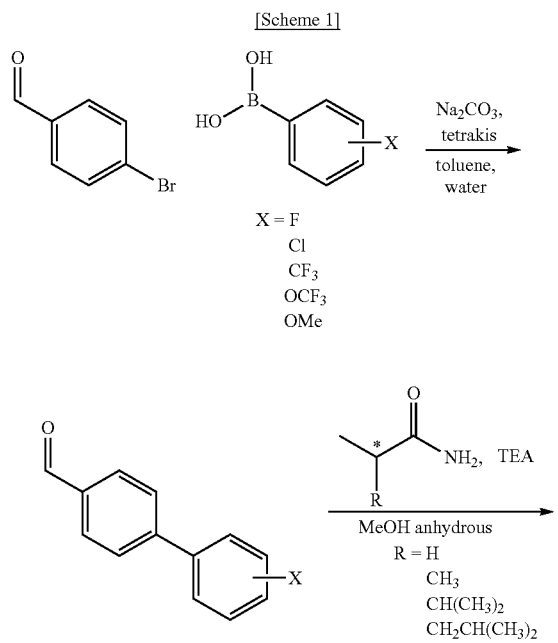

Because the compound has optical activity due to the carbon denoted by the asterisk (*), R- and S-compounds can be synthesized separately.

The present disclosure also provides a MAO-B (monoamine oxidase B) inhibitor containing the α-aminoamide derivative or a pharmaceutically acceptable salt or solvate thereof as an active ingredient.

The α-aminoamide derivative according to the present disclosure can be usefully used as a MAO-B inhibitor because it exhibits a superior effect of inhibiting the activity of monoamine oxidase B.

The present disclosure also provides a pharmaceutical composition for treating or preventing a neurodegenerative disease, which contains the α-aminoamide derivative or a pharmaceutically acceptable salt or solvate thereof as an active ingredient.

In the present disclosure, the neurodegenerative disease includes, for example, Parkinson's disease, Alzheimer's disease, etc., although not being limited thereto.

In another aspect, the present disclosure relates to a use of the α-aminoamide derivative according to various exemplary embodiments of the present disclosure or a pharmaceutically acceptable salt or solvate thereof for preparation of a drug for treating or preventing a neurodegenerative disease.

In another aspect, the present disclosure relates to a method for treating or preventing a neurodegenerative disease by administering a pharmaceutical composition containing the α-aminoamide derivative according to various exemplary embodiments of the present disclosure or a pharmaceutically acceptable salt or solvate thereof to a mammal.

The present disclosure also provides a γ-aminobutyric acid (GABA) production inhibitor containing the α-aminoamide derivative or a pharmaceutically acceptable salt or solvate thereof as an active ingredient.

The α-aminoamide derivative according to the present disclosure can be usefully used as a GABA production inhibitor because it can inhibit the production and secretion of GABA by inhibiting MAO-B which is an enzyme that produces GABA.

In addition, the α-aminoamide derivative according to the present disclosure can be usefully used as a pharmaceutical composition for treating or preventing obesity because it can exhibit a therapeutic effect for obesity by reliving the inhibition of or activating POMC neurons that selectively induces energy consumption and thereby promoting energy consumption.

Mode for Invention

Hereinafter, the present disclosure is described in detail through examples. However, the following examples are for illustrative purposes only and the scope and contents of the present disclosure should not be interpreted to be reduced or limited by the examples. In addition, it is obvious that those of ordinary skill can easily carry out the present disclosure based on the present disclosure including the examples even when experimental result is not provided specifically and that such modifications or changes fall within the scope of the appended claims.

Although the structures and physical properties of the compounds will vary depending on substituents, the principles and conditions of the reactions described in the examples can also be applied to the compounds having substituents not described in the examples and, therefore, it is obvious that those skilled in the art can easily derive the compounds having substituents based on the disclosure of the examples and the common knowledge of the related art.

EXAMPLES

Preparation Examples (1) Step (A)

4-Bromobenzaldehyde and boronic acid were subjected to Suzuki cross coupling reaction using a palladium catalyst as shown in [Scheme 1a]. Specifically, 4-bromobenzaldehyde (3 g, 16.21 mmol), boronic acid (1.28 equivalents), tetrakis(triphenylphosphine)palladium(0) (4-8 mol %) and sodium carbonate (4.86 equivalents) were refluxed in degassed toluene/distilled water (150 mL/21.6 mL) for 18 hours while heating. The reaction mixture was filtered through celite and the filtrate was washed twice with ethyl acetate (200 mL) and water (200 mL). The organic layer was combined and dried with sodium sulfate, concentrated in vacuo and then separated and purified by silica gel column chromatography.

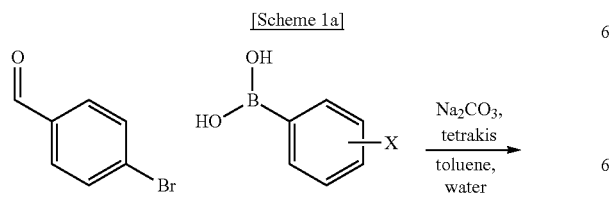

[Scheme 1a]

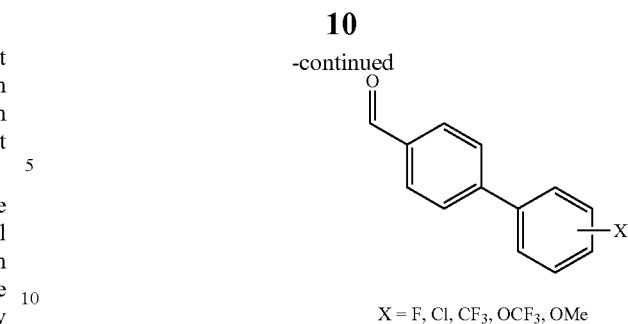

X = F, Cl, CF$_3$, OCF$_3$, OMe (2) Steps (B) and (C)

An imine compound was obtained by subjecting the compound of the step (A) to reductive amination using L-alaninamide hydrochloride or D-alaninamide hydrochloride (step (B), Scheme 1b). Then, an amine compound was obtained by reducing the imine compound with sodium cyanoborohydride (step (C), Scheme 1c).

After adding 1.2 equivalents of glycinamide hydrochloride or L-alaninamide hydrochloride or D-alaninamide hydrochloride or L-valinamide hydrochloride or L-leucinamide hydrochloride to anhydrous methanol to a concentration of 0.92 M, 1.5 equivalents of triethylamine was added. When the solution became transparent, 1.0 equivalent of the aldehyde synthesized in the step (A) was added. Two hours later, the solution was washed with ethyl acetate and distilled water. After drying the organic layer with sodium sulfate and drying in vacuo, the concentrated reaction solution was dissolved in anhydrous methanol to a concentration of 1.0 M and then 4.0 equivalents of sodium cyanoborohydride was added at 0° C. After performing reaction at room temperature for 18 hours, the reaction solution was washed with ethyl acetate and distilled water. The organic layer was dried with sodium sulfate, concentrated in vacuo and then separated and purified by silica gel column chromatography.

[Scheme 1b]

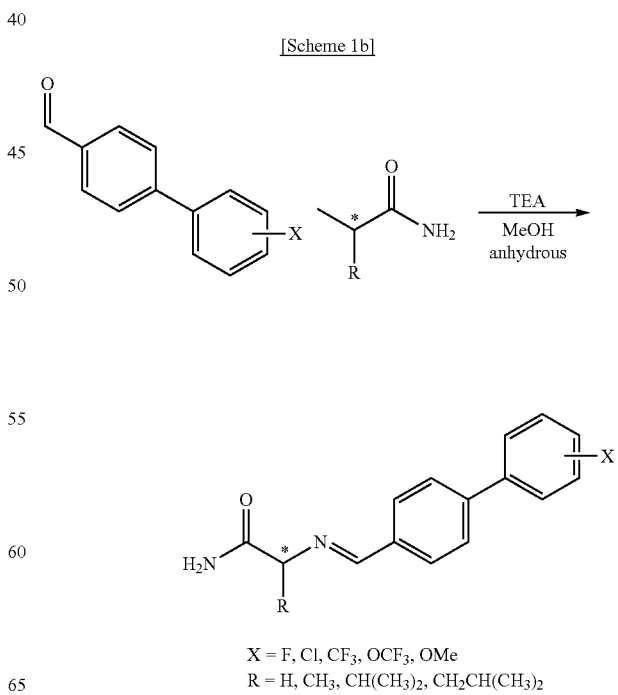

X = F, Cl, CF$_3$, OCF$_3$, OMe
R = H, CH$_3$, CH(CH$_3$)$_2$, CH$_2$CH(CH$_3$)$_2$

[Scheme 1c]

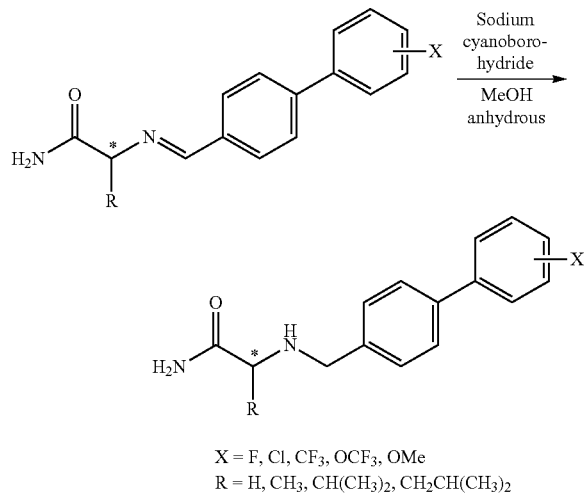

X = F, Cl, CF₃, OCF₃, OMe
R = H, CH₃, CH(CH₃)₂, CH₂CH(CH₃)₂

(3) Preparation of Salt

The salt preparation step is an optional step that can be either performed, if necessary, or omitted. A compound in salt form is synthesized to improve the solubility of the amine compound synthesized in the preceding step. The compound in salt form may be synthesized using an acid. The acid that can be used is described above but is not limited thereto.

Specifically, a compound in salt form was synthesized using methanesulfonic acid. After heating ethyl acetate to 50-55° C. and completely dissolving 1.0 equivalent of the compound of the step (C), 1.25 equivalents of methanesulfonic acid was added. 1 hour later, the reaction mixture was cooled to room temperature and filtered using a vacuum filtration device. The filtrate was washed with ethyl acetate and dried without a purification process.

[Scheme 1d]

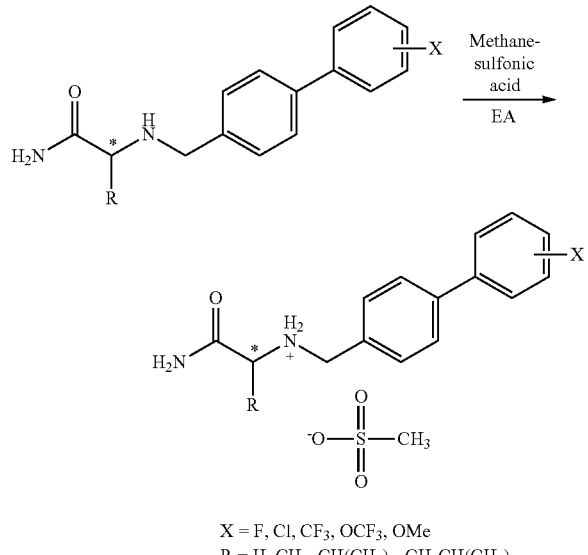

X = F, Cl, CF₃, OCF₃, OMe
R = H, CH₃, CH(CH₃)₂, CH₂CH(CH₃)₂

Example 1: Synthesis of (S)-2-(((2'-fluorobiphenyl-4-yl)methyl)amino) propanamide methanesulfonate

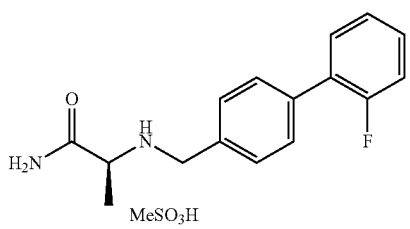 [SMILES: "MeSO3H" ; C[C@H](NCc1ccc(-c2ccccc2F)cc1)C(N)=O]

White solid; yield: 90%; ¹H NMR (300 MHz, DMSO-d₆) δ 9.17 (br s, 2H), 7.94 (br s, 1H), 7.30-7.94 (m, 9H), 4.16 (m, 2H), 3.80 (q, J=6.54 Hz, 1H), 2.30 (s, 3H), 1.45 (d, J=6.93 Hz, 3H); ¹³C NMR (75 MHz, DMSO-d₆) δ 170.9 (C(O)), 161.2, 157.9, 136.2, 131.7, 131.2, 131.1, 130.8, 130.5, 130.3, 129.5, 129.4, 128.1, 127.9, 125.5, 125.4, 116.8, 116.5 (ArC), 55.1 (C(O)CH⁺NH₂), 48.7 (⁺NH₂CH₂Ph), 16.4 (CH₃). SCH₃ signal overlapping with DMSO signal.

Example 2: Synthesis of (S)-2-(((3'-fluorobiphenyl-4-yl)methyl)amino) propanamide methanesulfonate

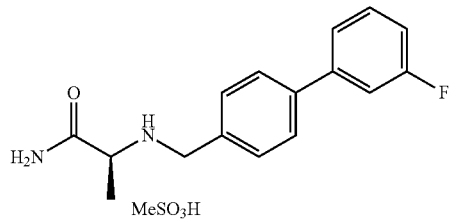 [SMILES: "MeSO3H" ; C[C@H](NCc1ccc(-c2cccc(F)c2)cc1)C(N)=O]

White solid; yield: 97%; ¹H NMR (300 MHz, DMSO-d₆) δ 9.15 (br s, 2H), 7.92 (br s, 1H), 7.81 (d, J=8.25 Hz, 2ArH), 7.68 (br s, 1H), 7.49-7.60 (m, 5ArH), 7.20-7.27 (m, 1ArH), 4.15 (s, 2H), 3.76 (q, J=9.24 Hz, 1H), 2.30 (s, 3H), 1.44 (d, J=9.28 Hz, 3H); ¹³C NMR (75 MHz, DMSO-d₆) δ 171.0 (C(O)), 164.9, 161.8, 161.6, 142.4, 142.3, 139.8, 132.0, 131.5, 131.4, 131.2, 127.5, 123.3, 115.2, 114.9, 114.1, 113.8 (ArC), 55.0 (C(O)CH⁺NH₂), 48.6 (⁺NH₂CH₂Ph), 16.4 (CH₃). SCH₃ signal overlapping with DMSO signal.

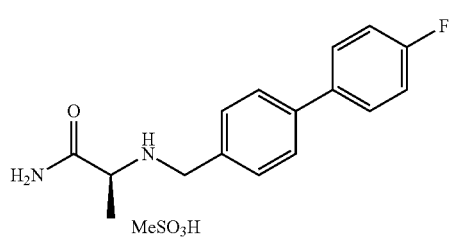 [SMILES: "MeSO3H" ; C[C@H](NCc1ccc(-c2ccc(F)cc2)cc1)C(N)=O]

White solid; yield: 88%; ¹H NMR (300 MHz, DMSO-d₆) δ 9.18 (br s, 2H), 7.95 (br s, 1H), 7.72-7.77 (m, 4ArH), 7.65 (br s, 1H), 7.56 (d, J=8.16 Hz, 2ArH), 7.28-7.34 (m, 2ArH), 4.12-4.15 (m, 2H), 3.78-3.84 (m, 1H), 2.37 (s, 3H), 1.45 (d, J=6.93 Hz, 3H); ¹³C NMR (75 MHz, DMSO-d₆) δ 171.0 (C(O)), 164.9, 161.8, 161.6, 142.4, 142.3, 139.8, 132.0, 131.5, 131.4, 131.2, 127.5, 123.3, 115.2, 114.9, 114.1, 113.8

(ArC), 55.0 (C(O)CH⁺NH₂), 48.6 (⁺NH₂CH₂Ph), 16.4 (CH₃). SCH₃ signal overlapping with DMSO signal.

Example 4: Synthesis of (S)-2-(((2'-chlorobiphenyl-4-yl)methyl)amino) propanamide methanesulfonate

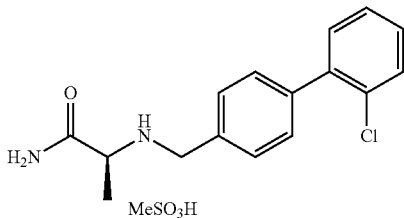 [SMILES: "MeSO3H" ; C[C@H](NCc1ccc(-c2ccccc2Cl)cc1)C(N)=O]

White solid; yield: 62%; ¹H NMR (300 MHz, DMSO-d₆) δ 9.18 (brs, ⁺NH₂), 7.96 (br s, 1C(O)NHH'), 7.67 (br s, 1C(O)NHH'), 7.59 (d, J=8.1 Hz, 3ArH), 7.52 (d, J=8.2 Hz, 2ArH), 7.39-7.47 (m, 3ArH), 4.09-4.28 (m, 2H), 3.86-3.90 (m, 1H), 2.30 (s, 3H), 1.47 (d, J=6.9 Hz, 3H); ¹³C NMR (75 MHz, DMSO-d₆) δ 170.9 (C(O)), 139.8, 139.6, 131.9, 131.8, 131.7, 130.4, 130.0, 128.1, 55.2 (C(O)CH⁺NH₂), 48.7 (⁺NH₂CH₂Ph), 16.4 (CH₃). SCH₃ signal overlapping with DMSO signal. Other peaks were not detected or seem to overlapping with other signals.

Example 5: Synthesis of (S)-2-(((3'-chlorobiphenyl-4-yl)methyl)amino) propanamide methanesulfonate

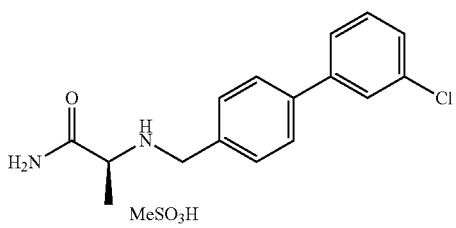 [SMILES: "MeSO3H" ; C[C@H](NCc1ccc(-c2cccc(Cl)c2)cc1)C(N)=O]

White solid; yield: 90%; ¹H NMR (400 MHz, DMSO-d₆) δ 9.16 (br s, 2H), 7.92 (br s, 1H), 7.81 (d, J=8.14 Hz, 2ArH), 7.77 (br s, 1H), 7.67-7.70 (m, 2ArH), 7.59 (d, J=8.14 Hz, 1ArH), 7.52 (t, J=7.88 Hz, 1ArH), 7.46 (d, J=8.1 Hz, 1ArH), 4.12-4.20 (m, 2H), 3.78 (d, J=6.7 Hz, 1H), 2.30 (s, 3H), 1.45 (d, J=6.7 Hz, 3H); ¹³C NMR (75 MHz, DMSO-d₆) δ 170.9 (C(O)), 141.9, 139.5, 134.3, 132.0, 131.3, 131.2, 128.7, 127.5, 126.9, 125.9 (ArC), 55.1 (C(O)CH⁺NH₂), 48.6 (⁺NH₂CH₂Ph), 16.4 (CH₃). SCH₃ signal overlapping with DMSO signal.

Example 6: Synthesis of (S)-2-((4'-chlorobiphenyl-4-yl)methyl)amino) propanamide methanesulfonate

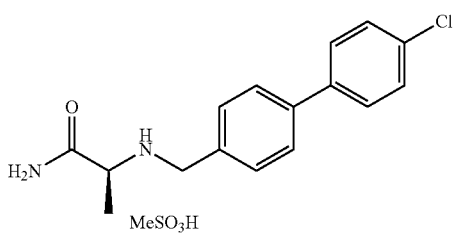 [SMILES: "MeSO3H" ; C[C@H](NCc1ccc(-c2ccc(Cl)cc2)cc1)C(N)=O]

White solid; yield: 84%; ¹H NMR (300 MHz, DMSO-d₆) δ 9.17 (br s, 1H), 7.94 (br s, 1H), 7.73-7.78 (m, 4ArH), 7.66 (br s, 1H), 7.53-7.60 (m, 4ArH), 4.10-4.20 (m, 2H), 3.76-3.82 (m, 1H), 2.32 (s, 3H), 1.45 (d, J=6.93 Hz, 3H); ¹³C NMR (100 MHz, DMSO-d₆) δ 170.9 (C(O)), 139.9, 138.6, 133.2, 131.7, 131.2, 129.5, 129.4, 129.0, 127.3 (ArC), 54.9, (C(O)CH⁺NH₂), 48.5 (⁺NH₂CH₂Ph), 16.3 (CH₃). SCH₃ signal overlapping with DMSO signal.

Example 7: Synthesis of (S)-2-(((2'-trifluoromethyl-biphenyl-4-yl)methyl)amino) propanamide methanesulfonate

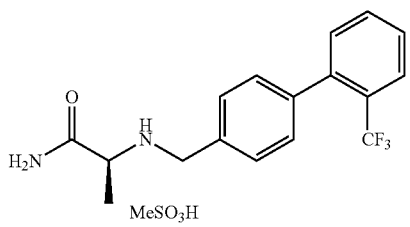 [SMILES: "MeSO3H" ; C[C@H](NCc1ccc(-c2ccccc2C(F)(F)F)cc1)C(N)=O]

White solid; yield: 87%; ¹H NMR (300 MHz, DMSO-d₆) δ 9.20 (br s, ⁺NH₂), 7.94 (br s, 1C(O)NHH'), 7.85 (d, J=7.8 Hz, 1ArH), 7.75 (t, J=7.4 Hz, 1ArH), 7.61-7.67 (m, 2ArH), 7.57 (d, J=7.2 Hz, 1ArH), 7.39-7.41 (m, 2ArH, 1C(O)NHH'), 4.11-4.22 (m, 2H), 3.86-3.88 (m, 1H), 2.32 (s, 3H), 1.47 (d, J=6.7 Hz, 3H); ¹³C NMR (75 MHz, DMSO-d₆) δ 170.9 (C(O)), 140.5, 140.4, 132.8, 132.5, 131.9, 130.1, 129.4, 128.7, 127.3 (q, $J_{C-F}$=29.2 Hz), 126.5 (q, $J_{C-F}$=5.2 Hz), 124.6 (q, $J_{C-F}$=270.5 Hz), 55.4 (C(O)CH⁺NH₂), 48.8 (⁺NH₂CH₂Ph), 40.2 (SCH₃), 16.4 (CH₃).

Example 8: Synthesis of (S)-2-(((3'-trifluoromethyl-biphenyl-4-yl)methyl)amino) propanamide methanesulfonate

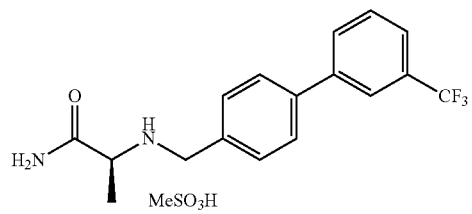 [SMILES: "MeSO3H" ; C[C@H](NCc1ccc(-c2cccc(C(F)(F)F)c2)cc1)C(N)=O]

White solid; yield: 92%; ¹H NMR (400 MHz, DMSO-d₆) δ 9.16 (br s, 2H), 7.988.02 (m, 2ArH), 7.90 (br s, 1H), 7.84 (d, J=8.10 Hz, 2ArH), 7.69-7.76 (m, 2ArH), 7.65 (br s, 1H), 7.59 (d, J=8.10 Hz, 2ArH), 4.14 (m, 2H), 3.76 (d, J=5.36 Hz, 1H), 2.27 (S, 3H), 1.43 (d, J=6.88 Hz, 3H); ¹³C NMR (100 MHz, DMSO-d₆) δ 170.9 (C(O)), 140.9, 139.5, 132.2, 131.3, 131.2, 130.7, 130.5, 130.2, 129.9, 128.7, 127.7, 126.0, 124.8, 123.6, 123.3 (ArC), 55.0 (C(O)CH⁺NH₂), 48.5 (⁺NH₂CH₂Ph), 16.4 (CH₃). SCH₃ signal overlapping with DMSO signal.

Example 9: Synthesis of (S)-2-(((4'-trifluoromethyl-biphenyl-4-yl)methyl)amino) propanamide methanesulfonate

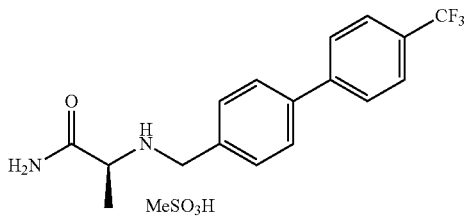 [SMILES: "MeSO3H" ; C[C@H](NCc1ccc(-c2ccc(C(F)(F)F)cc2)cc1)C(N)=O]

White solid; yield: 82%; $^1$H NMR (300 MHz, DMSO-$d_6$) δ 9.17 (br s, 2H), 7.93-7.96 (m, 3H), 7.84 (d, J=7.65 Hz, 4H), 7.63-7.66 (m, 3H), 4.12-4.23 (m, 2H), 3.78-3.83 (m, 1H), 2.32 (s, 3H), 1.46 (d, J=6.93 Hz, 3H); $^{13}$C NMR (75 MHz, DMSO-$d_6$) δ 170.9 (C(O)), 143.8, 139.6, 132.4, 131.3, 128.8, 128.4, 128.0, 127.8, 126.6, 126.3, 126.2, 123.0 (ArC), 54.9 (C(O)CH$^+$NH$_2$), 48.5 ($^+$NH$_2$CH$_2$Ph), 16.4 (CH$_3$). SCH$_3$ signal overlapping with DMSO signal.

Example 10: Synthesis of (S)-2-(((3'-trifluoromethoxybiphenyl-4-yl)methyl) amino)propanamide methanesulfonate

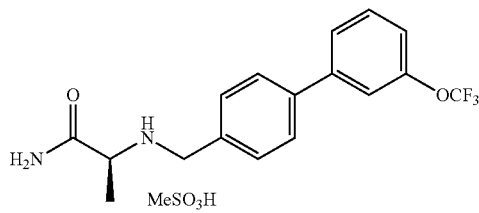 [SMILES: "MeSO3H" ; C[C@H](NCc1ccc(-c2cccc(OC(F)(F)F)c2)cc1)C(N)=O]

White solid; yield: 90%; $^1$H NMR (300 MHz, DMSO-$d_6$) δ 9.16 (br s, 2H), 7.92 (br s, 1H), 7.83 (d, J=8.22 Hz, 2ArH), 7.77 (d, J=8.22 Hz, 1ArH), 7.59-7.69 (m, 5H), 7.39-7.42 (m, 1ArH), 4.16 (s, 2H), 3.77 (q, J=7.08 Hz, 1H), 2.30 (s, 3H), 1.44 (d, J=6.99 Hz, 3H); $^{13}$C NMR (100 MHz, DMSO-$d_6$) δ 170.9 (C(O)), 149.5, 142.2, 139.4, 132.2, 131.5, 131.3, 131.2, 127.6, 126.3, 124.4, 121.9, 120.5, 119.8, 119.7, 119.3 (ArC), 55.0, (C(O)CH$^+$NH$_2$), 48.5 ($^+$NH$_2$CH$_2$Ph), 16.4 (CH$_3$). SCH$_3$ signal overlapping with DMSO signal.

Example 11: Synthesis of (S)-2-(((4'-trifluoromethoxybiphenyl-4-yl)methyl) amino)propanamide methanesulfonate

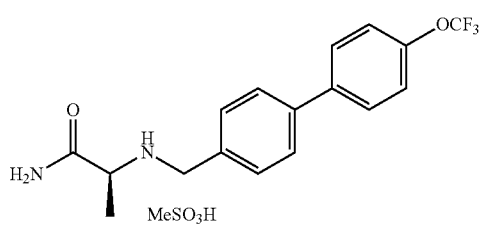 [SMILES: "MeSO3H" ; C[C@H](NCc1ccc(-c2ccc(OC(F)(F)F)cc2)cc1)C(N)=O]

White solid; yield: 92%; $^1$H NMR (400 MHz, DMSO-$d_6$) δ 9.17 (br s, 2H), 7.92 (br s, 1H), 7.83 (d, J=8.68 Hz, 2ArH), 7.78 (d, J=8.16 Hz, 2ArH), 7.67 (br s, 1H), 7.59 (d, J=8.12 Hz, 2ArH), 7.48 (d, J=8.20 Hz, 2ArH), 4.16 (s, 2H), 3.78 (s, 1H), 2.30 (s, 3H), 1.44 (d, J=6.96 Hz, 3H); $^{13}$C NMR (100 MHz, DMSO-$d_6$) δ 170.9 (C(O)), 148.5, 139.7, 139, 131.8, 131.3, 131.2, 129.2, 129.1, 127.6, 127.5, 124.4, 122.1, 121.9, 121.8, 119.8, 116.7 (ArC), 55.3, 55.1, 54.9, 54.7 (C(O)CH$^+$NH$_2$), 48.6 ($^+$NH$_2$CH$_2$Ph), 16.4 (CH$_3$). SCH$_3$ signal overlapping with DMSO signal.

Example 12: Synthesis of (S)-2-(((3'-methoxybiphenyl-4-yl)methyl) amino)propanamide methanesulfonate

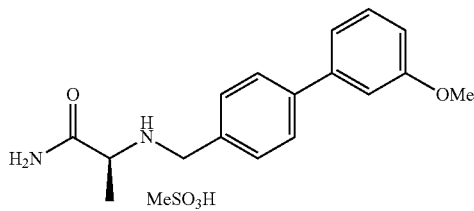 [SMILES: "MeSO3H" ; COc1cccc(-c2ccc(CN[C@@H](C)C(N)=O)cc2)c1]

White solid; yield: 91%; $^1$H NMR (400 MHz, DMSO-$d_6$) δ 9.14 (br s, 2H), 7.91 (br s, 1H), 7.76 (d, J=8.16 Hz, 2ArH), 7.66 (br s, 1H), 7.66 (br s, 1H), 7.40 (t, J=7.92 Hz, 3ArH), 7.26 (d, J=7.76 Hz, 1ArH), 7.21 (m, 1ArH), 6.95-6.98 (m, 1ArH), 4.14 (m, 2H), 3.83 (s, 3H), 3.77 (q, J=6.96 Hz, 1H), 2.30 (S, 3H), 1.44 (d, J=6.96 Hz, 3H); $^{13}$C NMR (75 MHz, DMSO-$d_6$) δ 170.9 (C(O)), 160.3, 141.3, 141.1, 131.4, 131.1, 130.6, 127.4, 119.5, 113.8, 112.7 (ArC), 55.6, 54.9 (C(O)CH$^+$NH$_2$), 48.6 ($^+$NH$_2$CH$_2$Ph), 16.4 (CH$_3$). SCH$_3$ signal overlapping with DMSO signal.

Example 13: Synthesis of (S)-2-(((4'-methoxybiphenyl-4-yl)methyl) amino)propanamide methanesulfonate

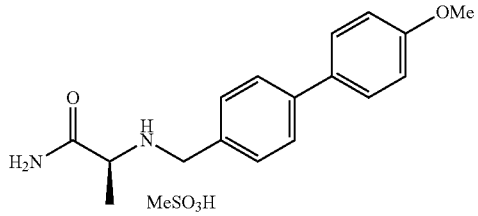 [SMILES: "MeSO3H" ; COc1ccc(-c2ccc(CN[C@@H](C)C(N)=O)cc2)cc1]

White solid; yield: 84%; $^1$H NMR (300 MHz, DMSO-$d_6$) δ 9.14 (br s, 2H), 7.92 (br s, 1H), 7.64-7.72 (m, 5H), 7.54 (d, J=8.25 Hz, 2H), 7.04 (d, J=8.79 Hz, 2ArH), 4.13 (s, 2H), 3.72-3.89 (m, 4H), 2.31 (s, 3H), 1.44 (d, J=6.96 Hz, 3H); $^{13}$C NMR (75 MHz, DMSO-$d_6$) δ 170.9 (C(O)), 159.6, 140.9, 132.1, 131.0, 128.4, 128.2, 126.8, 115.2, 115.0, 114.8, 114.6 (ArC), 55.8, 55.6, 54.9, 54.8 (C(O)CH$^+$NH$_2$), 48.7 ($^+$NH$_2$CH$_2$Ph), 16.4 (CH$_3$). SCH$_3$ signal overlapping with DMSO signal.

Example 14: Synthesis of (R)-2-(((3'-fluoromethoxybiphenyl-4-yl)methyl) amino)propanamide methanesulfonate

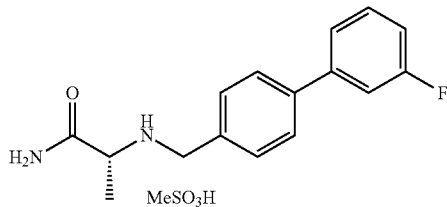 [SMILES: "MeSO3H" ; C[C@@H](NCc1ccc(-c2cccc(F)c2)cc1)C(N)=O]

White solid; yield: 87%; $^1$H NMR (300 MHz, DMSO-$d_6$) δ 9.16 (br s, 2H), 7.93 (br s, 1H), 7.81 (d, J=8.07 Hz, 2H), 7.67 (br s, 1H), 7.49-7.60 (m, 5ArH), 7.23 (m, 1H), 4.15-4.20 (m, 2H), 3.79 (q, J=6.93 Hz, 1H), 2.30 (s, 3H), 1.44 (d, J=6.90 Hz, 3H); $^{13}$C NMR (75 MHz, DMSO-$d_6$) δ 170.9, (C(O)), 164.8, 161.6, 142.3, 142.2, 139.7, 139.6, 132.0, 131.5, 131.4, 131.2, 127.5, 123.3, 123.2, 115.1, 114.8, 114.0, 113.7 (ArC), 55.0 (C(O)CH$^+$NH$_2$), 48.6 ($^+$NH$_2$CH$_2$Ph), 16.4 (CH$_3$). SCH$_3$ signal overlapping with DMSO signal.

Example 15: Synthesis of (R)-2-(((4'-trifluoromethylbiphenyl-4-yl)methyl) amino)propanamide methanesulfonate

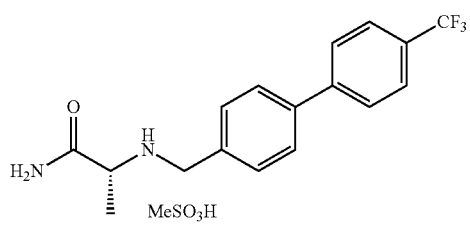 [SMILES: "MeSO3H" ; C[C@@H](NCc1ccc(-c2ccc(C(F)(F)F)cc2)cc1)C(N)=O]

White solid; yield: 87%; $^1$H NMR (300 MHz, DMSO-$d_6$) δ 9.18 (br s, 2H), 7.93-7.95 (m, 3H), 7.84 (d, J=7.89 Hz, 4H), 7.62-7.66 (m, 3H), 4.12-4.22 (m, 2H), 3.80 (q, J=6.27 Hz, 1H), 2.31 (s, 3H), 1.45 (d, J=6.78 Hz, 3H); $^{13}$C NMR (75 MHz, DMSO-$d_6$) δ 170.9 (C(O)), 143.8, 139.5, 132.4, 131.3, 130.2, 129.2, 128.8, 128.4, 128.0, 127.7, 126.6, 126.3, 126.2, 123.0, 119.4 (ArC), 55.1 (C(O)CH$^+$NH$_2$), 48.6 ($^+$NH$_2$CH$_2$Ph), 16.4 (CH$_3$). SCH$_3$ signal overlapping with DMSO signal.

Example 16: Synthesis of (R)-2-(((4'-trifluoromethylbiphenyl-4-yl)methyl) amino)acetamide methanesulfonate

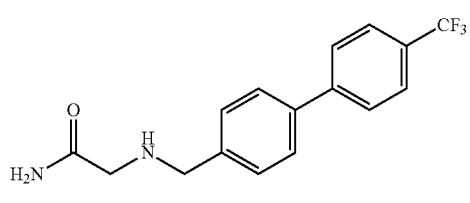

White solid; yield: 90%; $^1$H NMR (300 MHz, DMSO-$d_6$) δ 9.26 (br s, $^+$NH$_2$), 7.91-7.93 (m, 2ArH, 1C(O)NHH'), 7.79-7.82 (m, 4ArH), 7.65 (d, J=7.2 Hz, 2ArH), 7.58 (br s, C(O)NHH'), 4.25 (s, 2H), 3.71 (s, 2H), 2.40 (s, 3H); $^{13}$C NMR (75 MHz, DMSO-$d_6$) δ 167.3 (C(O)), 143.8, 139.6, 132.3, 131.4, 128.6 (q, $J_{C-F}$=31.7 Hz), 128.0, 127.7, 126.3 (q, $J_{C-F}$=3.7 Hz), 124.8 (q, $J_{C-F}$=270.2 Hz) (ArC), 49.9 (C(O)CH$^+$NH$_2$), 47.3 ($^+$NH$_2$CH$_2$Ph), 40.1 (SCH$_3$).

Example 17: Synthesis of (R)-3-methyl-2-(((4'-trifluoromethylbiphenyl-4-yl) methyl)amino)butanamide methanesulfonate

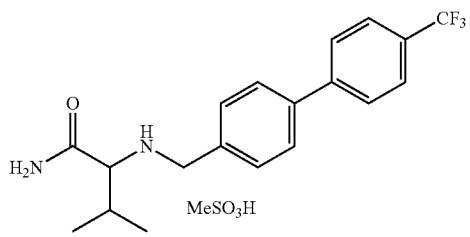 [SMILES: "MeSO3H" ; CC(C)C(NCc1ccc(-c2ccc(C(F)(F)F)cc2)cc1)C(N)=O]

White solid; yield: 74%; $^1$H NMR (300 MHz, DMSO-$d_6$) δ 9.20 (br s, $^+$NHH'), 8.95 (br s, $^+$NHH'), 7.78-7.96 (m, 6ArH, C(O)NH$_2$), 7.60-7.65 (m, 2ArH), 4.02-4.18 (m, 2H), 3.47-3.69 (m, 1H), 2.30 (s, 3H), 2.16-2.22 (m, 1H), 0.92-1.00 (m, 6H); $^{13}$C NMR (75 MHz, DMSO-$d_6$) δ 168.4 (C(O)), 143.8, 139.6, 131.8, 131.7, 128.6 (q, $J_{C-F}$=31.8 Hz), 126.3 (q, $J_{C-F}$=3.7 Hz), 124.8 (q, $J_{C-F}$=270.2 Hz), 64.1 (C(O)CH$^+$NH$_2$), 49.7 ($^+$NH$_2$CH$_2$Ph), 40.2 (SCH$_3$), 29.3 (CHCH$_2$), 19.1 (CH$_3$), 18.1 (CH$_3$).

Example 18: Synthesis of (R)-4-methyl-2-(((4'-trifluoromethylbiphenyl-4-yl) methyl)amino)pentanamide methanesulfonate

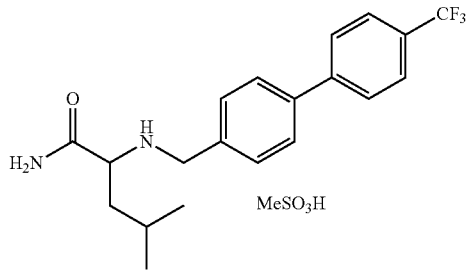 [SMILES: "MeSO3H" ; CC(C)CC(NCc1ccc(-c2ccc(C(F)(F)F)cc2)cc1)C(N)=O]

White solid; yield: 77%; $^1$H NMR (300 MHz, DMSO-$d_6$) δ 9.30 (br s, $^+$NHH'), 9.16 (br s, $^+$NHH'), 8.13 (br s, C(O)NHH'), 7.94 (d, J=7.85 Hz, 2ArH), 7.84 (d, J=7.80 Hz, 4ArH), 7.79 (br s, C(O)NHH'), 7.63 (d, J=7.85 Hz, 2ArH), 4.05-4.25 (m, 2H), 3.70-3.83 (m, 1H), 2.35 (s, 3H), 1.59-1.79 (m, 1CH, 2CHCH$_2$), 0.80-1.03 (m, 6H); $^{13}$C NMR (75 MHz, DMSO-$d_6$) δ 169.9 (C(O)), 143.8, 139.6, 132.2, 131.4, 128.6 (q, $J_{C-F}$=31.9 Hz), 128.4, 127.7, 126.3 (q, $J_{C-F}$=3.7 Hz), 124.8 (q, $J_{C-F}$=270.3 Hz), 58.4 (C(O)CH$^+$NH$_2$), 49.0 ($^+$NH$_2$CH$_2$Ph), 40.2 (SCH$_3$), 24.4, 23.5, 22.3.

Test Example 1. Effect of Inhibiting Activity of Monoamine Oxidase B (MAO-B Assay)

(A) 10 mM of the compound was prepared into 5 concentrations of 1 mM, 0.1 mM, 0.01 mM, 0.001 mM and 0.0001 mM by serially diluting 10-fold and a 0.05 M sodium phosphate (pH 7.4) buffer was prepared.

(B) 5 mg/mL of human-derived monoamine oxidase B was diluted to 1/200 with a 0.05 M sodium phosphate buffer and enzyme buffers were prepared by mixing with 2 μL of the compound solutions of 5 concentrations to a final volume of 100 μL. The enzyme buffer was added to a 96-well plate and reaction was performed for 1 hour.

(C) After mixing 100 μL of a working buffer prepared by adding 20 mM Amplex Red (200 μL), 100 mM benzylamine substrate (200 μL) and 200 U/mL horseradish peroxidase (100 μL) to a 0.05 M sodium phosphate (pH 7.4) buffer (9.5 mL) with the enzyme buffer of (B) at 1:1 and conducting incubation for 2 hours, absorbance was measured (570 nm). The determined activity of the compounds of the present disclosure is shown in Table 1.

Safinamide well known as a reversible MAO-B inhibitor was used as a control. As seen from [Chemical Formula 2], safinamide has a structure in which a benzyloxyphenyl group instead of a biphenyl group is attached to the α-aminoamide according to the present disclosure.

[Chemical Formula 2]

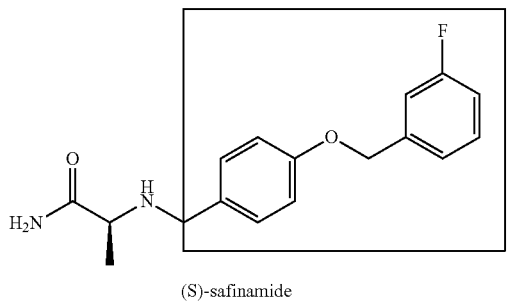

(S)-safinamide

Safinamide is well known as a substance that exhibits superior MAO-B inhibiting effect and efficacy in animals. However, it is limited to be used as a selective MAO-B inhibitor because it also acts as a calcium channel and sodium channel inhibitor.

TABLE 1

| | Stereo | R | X | MAO-B (IC$_{50}$, μm) | MAO-A (IC$_{50}$, μm) |
|---|---|---|---|---|---|
| Example 1 | S | CH$_3$ | 2'-F | >10 | >100 |
| Example 2 | S | CH$_3$ | 3'-F | >10 | >100 |
| Example 3 | S | CH$_3$ | 4'-F | >10 | >100 |
| Example 4 | S | CH$_3$ | 2'-Cl | >10 | >100 |
| Example 5 | S | CH$_3$ | 3'-Cl | 0.442 | >100 |
| Example 6 | S | CH$_3$ | 4'-Cl | 0.416 | >100 |
| Example 7 | S | CH$_3$ | 2'-CF$_3$ | >10 | >100 |
| Example 8 | S | CH$_3$ | 3'-CF$_3$ | 0.316 | >100 |
| Example 9 | S | CH$_3$ | 4'-CF$_3$ | 0.042 | >500 |
| Example 10 | S | CH$_3$ | 3'-OCF$_3$ | 0.216 | >100 |
| Example 11 | S | CH$_3$ | 4'-OCF$_3$ | 0.098 | >100 |
| Example 12 | S | CH$_3$ | 3'-OCH$_3$ | 3.33 | >100 |
| Example 13 | S | CH$_3$ | 4'-OCH$_3$ | 1.06 | >100 |
| Example 14 | R | CH$_3$ | 3'-F | >10 | >100 |
| Example 15 | R | CH$_3$ | 4'-CF$_3$ | 0.082 | >100 |
| Example 16 | S | H | 4'-CF$_3$ | 0.126 | >100 |
| Example 17 | S | CH(CH$_3$)$_2$ | 4'-CF$_3$ | 4.073 | >100 |
| Example 18 | S | CH$_2$CH(CH$_3$)$_2$ | 4'-CF$_3$ | 5.302 | >100 |
| S-Safinamide | — | — | — | 0.12 | >100 |
| Selegilne | — | — | — | 0.009 | ~1 |

As can be seen from Table 1, when various functional groups were introduced to the position X of the biphenyl group, better activity was achieved when the functional group was introduced to the para position as compared to the ortho or meta position and excellent inhibitory effect was achieved when —CF$_3$ or —OCF$_3$ was introduced as compared to when F or Cl was introduced. In particular, the compound of Example 9 showed the best activity which is 2 times or higher than that of safinamide. Although the compound of Example 15, which is a stereoisomer of the compound of Example 9, also showed superior activity, its activity was slightly lower than that of the compound of Example 9. In addition, alkyl groups such as hydrogen, isopropyl and isobutyl were introduced instead of the methyl group at the position R. Whereas the compound of Example 16 wherein hydrogen was introduced showed slightly decreased activity, significantly decreased activity was observed when isopropyl and isobutyl groups which are larger than the methyl group were introduced.

Also, the cytotoxicity and passage through the blood-brain barrier (BBB) of the compounds of the examples according to the present disclosure were investigated. The followings were confirmed.

(1) The position of the substituent X is preferable in the order of pare, meta and ortho. In particular, the para position is the most preferable in terms of MAO-B inhibition activity and the effect of remarkably reducing antibody-dependent cellular cytotoxicity can be achieved additionally as compared to the ortho and meta positions.

(2) As the substituent X, —OCF$_3$, —CF$_3$ and —Cl showed superior MAO-B inhibition activity. In particular, —OCF$_3$ or —CF$_3$ showed better MAO-B inhibition activity than —Cl, —OCH$_3$ or —F and the effect of allowing easy passage through the blood-brain barrier can be achieved additionally.

(3) The S-isomer showed better MAO-B inhibition activity and remarkably superior recovery of MAO-B activity as compared to the R-isomer. In addition, good metabolic stability and significantly low cytotoxicity can be achieved additionally.

(4) As the substituent R, —CH$_3$ and —H showed superior MAO-B activity. In particular, —CH$_3$ exhibits better MAO-B activity than —H, —CH(CH$_3$)$_2$ or —CH$_2$CH(CH$_3$)$_2$ and the effect of allowing easy passage through the blood-brain barrier can be achieved additionally.

Hereinafter, test examples were performed on the compound of Example 9 as a representative example of the compounds to confirm efficacy. It is obvious that the same tests can be conducted on other compounds based on the description of the present disclosure.

Test Example 2: Confirmation of Reversible Inhibitory Effect

Reversible inhibitory effect was investigated according to the method described in FIG. 1.

An enzyme buffer was prepared by diluting 5 mg/mL of human-derived monoamine oxidase B with a 0.05 M sodium phosphate (pH 7.4) buffer to 1/40. After mixing 441 μL of the enzyme buffer with 9 μL of the compound of Example 9 (0.1 mM), reaction was performed for 2 hours.

The reaction solution was divided into two, with 200 μL each. One was transferred to a 96-well plate (A) and the remainder was centrifuged at 14,000 g for 20 minutes in a centrifugal filter (Amicon® Ultra-3K) (B). After adding 500 μL of a 0.05 M sodium phosphate (pH 7.4) buffer to the centrifugal filter, centrifugation was performed at 14,000 g for 20 minutes. This procedure was repeated 2 times.

The human-derived monoamine oxidase B remaining in the centrifugal fitter was diluted by adding 200 μL of a 0.05 M sodium phosphate (pH 7.4) buffer to the centrifugal filter and then transferred to a 96-well plate. Then, 100 μL of a working buffer prepared by adding 20 mM Amplex Red (200 μL), 100 mM benzylamine substrate (200 μL) and 200 U/mL horseradish peroxidase (100 μL) to a 0.05 M sodium phosphate (pH 7.4) buffer (9.5 mL) was mixed with the enzyme buffer at 1:1 and absorbance was measured (570 nm) after conducting incubation for 2 hours.

Selegiline well known as an irreversible MAO-B inhibitor was used as a control to test the reversibility of the compound of the present disclosure. The result is shown in Table 2.

TABLE 2

|  | Dose | A. MAO-B inhibition effect | B. MAO-B inhibition effect | Recovered MAO-B activity | Reversibility |
| --- | --- | --- | --- | --- | --- |
| Selegiline | 1 μM | >90% | >90% | 0% | Irreversible |
| Example 9 | 1 μM | 82% | <15% | >85% | Reversible |

As seen from Table 2, both compounds showed 80% or higher inhibitory effect at 1 μM. When the activity of MAO-B was measured again after washing 3 times with a buffer, the irreversible inhibitor selegiline maintained its inhibitory effect but the compound of the present disclosure showed no inhibitory effect because it was washed off during the washing procedure. The fact that the activity of MAO-B was recovered as the inhibitory compound was washed off reveals that the compound of the present disclosure is a reversible inhibitor.

Test Example 3: Efficacy of Compound 9 in MPTP Mouse Model of Parkinson's Disease The efficacy of compound 9 in the MPTP mouse model of Parkinson's disease was compared with that of the existing MAO-B inhibitor safinamide. 20 mg/kg of MPTP was injected intraperitoneally in order to induce Parkinson's disease and 10 mg/kg of MAO-B inhibitors including compound 9 were administered orally. First, the MAO-B inhibitor was administered for 3 days starting from one day before the injection of the MPTP and its effect was analyzed quantitatively by an immunohistochemical method using TH (tyrosine hydroxylase) as a marker for dopaminergic neurons. As the brain parts for analysis, the substantia nigra and the corpus striatum where dopaminergic neurons are present were selected. It is well known that the expression of TH in these regions decreases significantly in Parkinson's disease. In the following experiments, it was investigated whether compound 9 protects dopaminergic neurons from MPTP by inhibiting MAO-B.

(1) First, after treating once with compound 9, its efficacy in the MPTP-treated mouse model was tested.

Figure 2A:
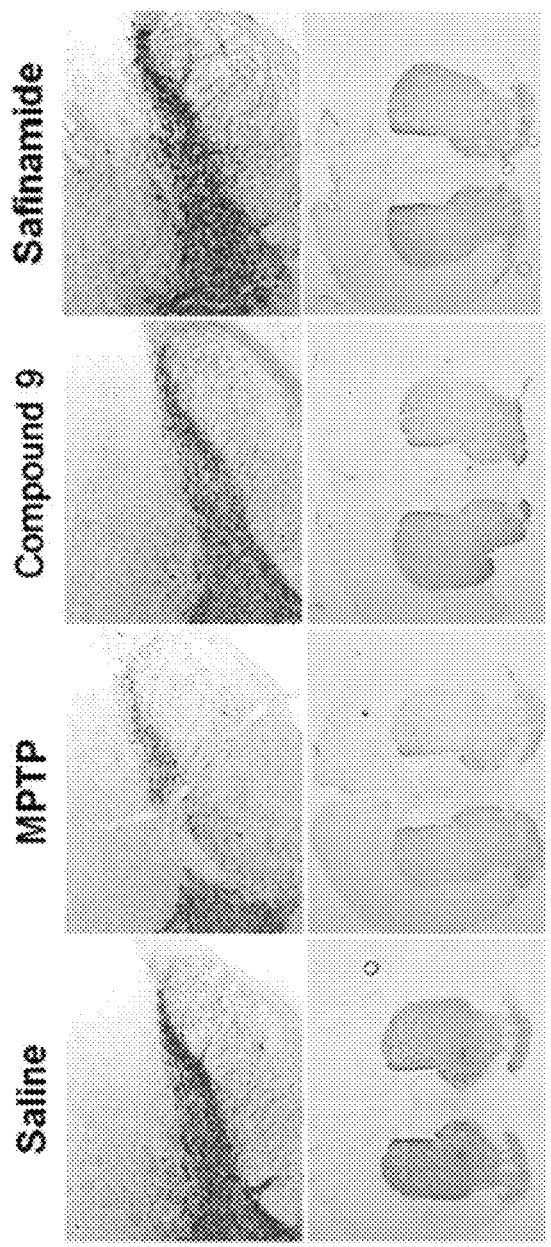
FIG. 2a shows the dopaminergic neuron protecting effect of compound 9 in the substantia nigra and the corpus striatum (pre-treatment).
Figure 2A:
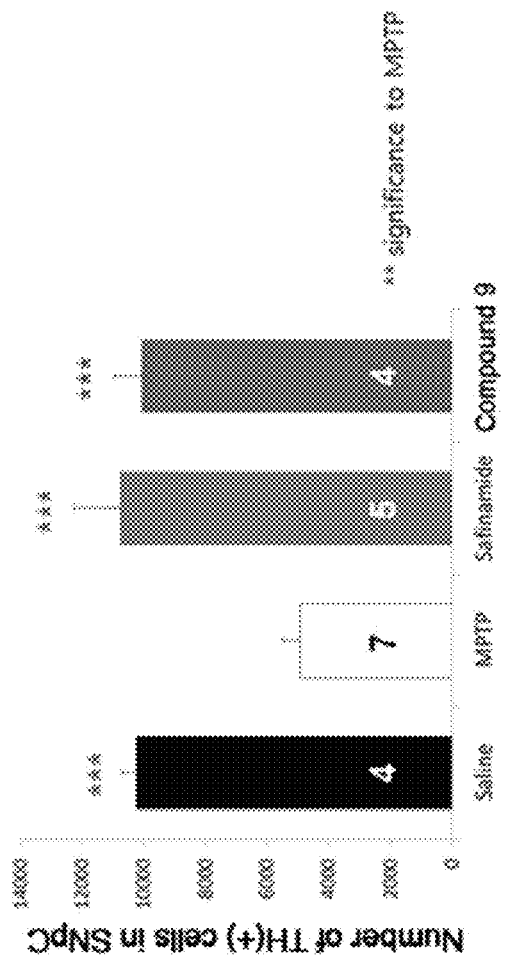
Figure 2A:
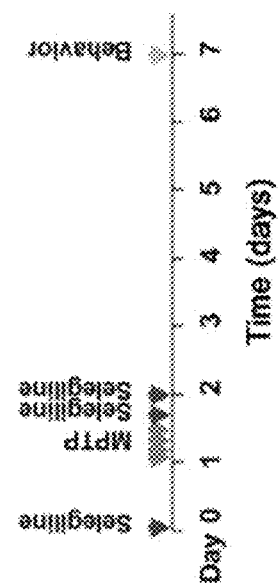

As seen from FIG. 2a, the expression of TH was remarkably decreased in the model treated only with MPTP after the tyrosine hydroxylase staining as compared to the control group (saline), which suggests that the number of dopaminergic neurons was decreased remarkably. However, the models treated with the MAO-B inhibitors safinamide and compound 9 showed dopaminergic neuron survivability comparable to that of the control group.

(2) Next, after establishing a MPTP mouse model by treating with MPTP, the compound was treated from day 3 and it was observed whether the dopaminergic neurons were recovered in the Parkinson's disease animal model due to inhibition of MAO-B.

Figure 2B:
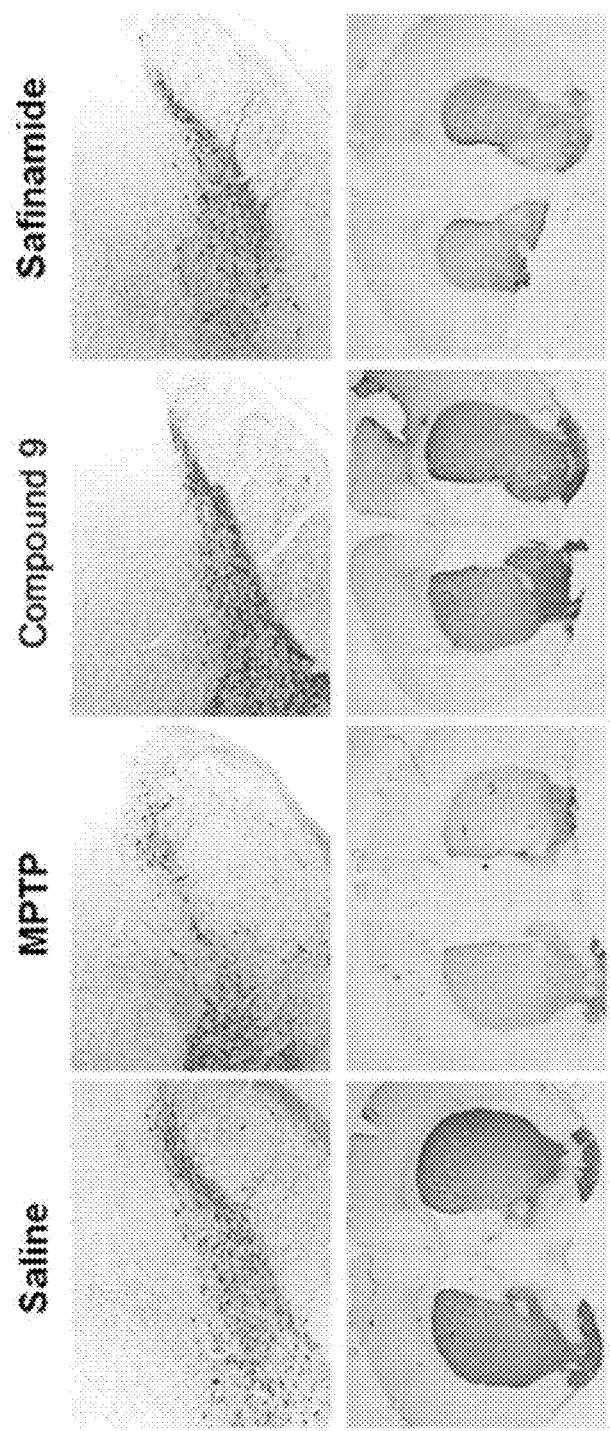
FIG. 2b shows the dopaminergic neuron protecting effect of compound 9 in the substantia nigra and the corpus striatum (post-treatment).
Figure 2B:
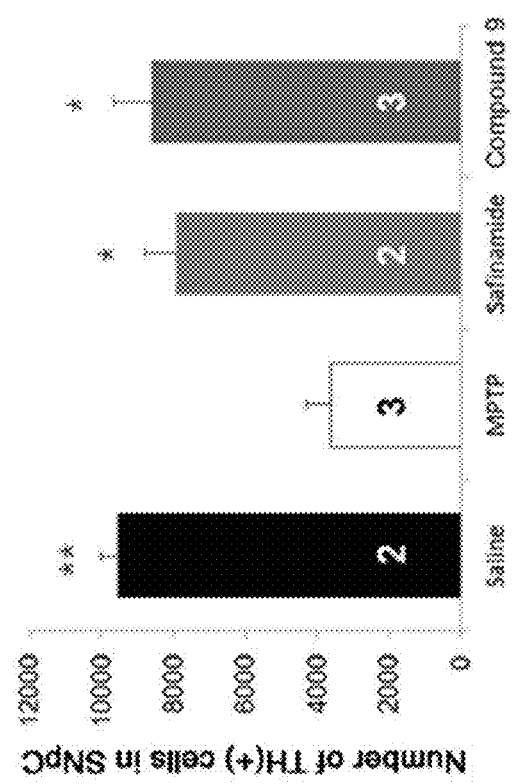
Figure 2B:
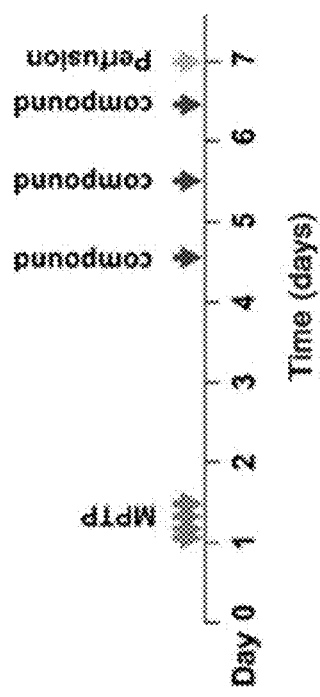

As seen from FIG. 2b, the neurons were destroyed in the MPTP-treated group as in the pre-treatment experiment. In contrast, the models treated with the MAO-B inhibitors safinamide and compound 9 showed significantly decreased death of the neurons. In particular, compound 9 recovered the dopaminergic neurons in the substantia nigra to a level comparable to that of the control group not treated with MPTP.

Figure 2C:
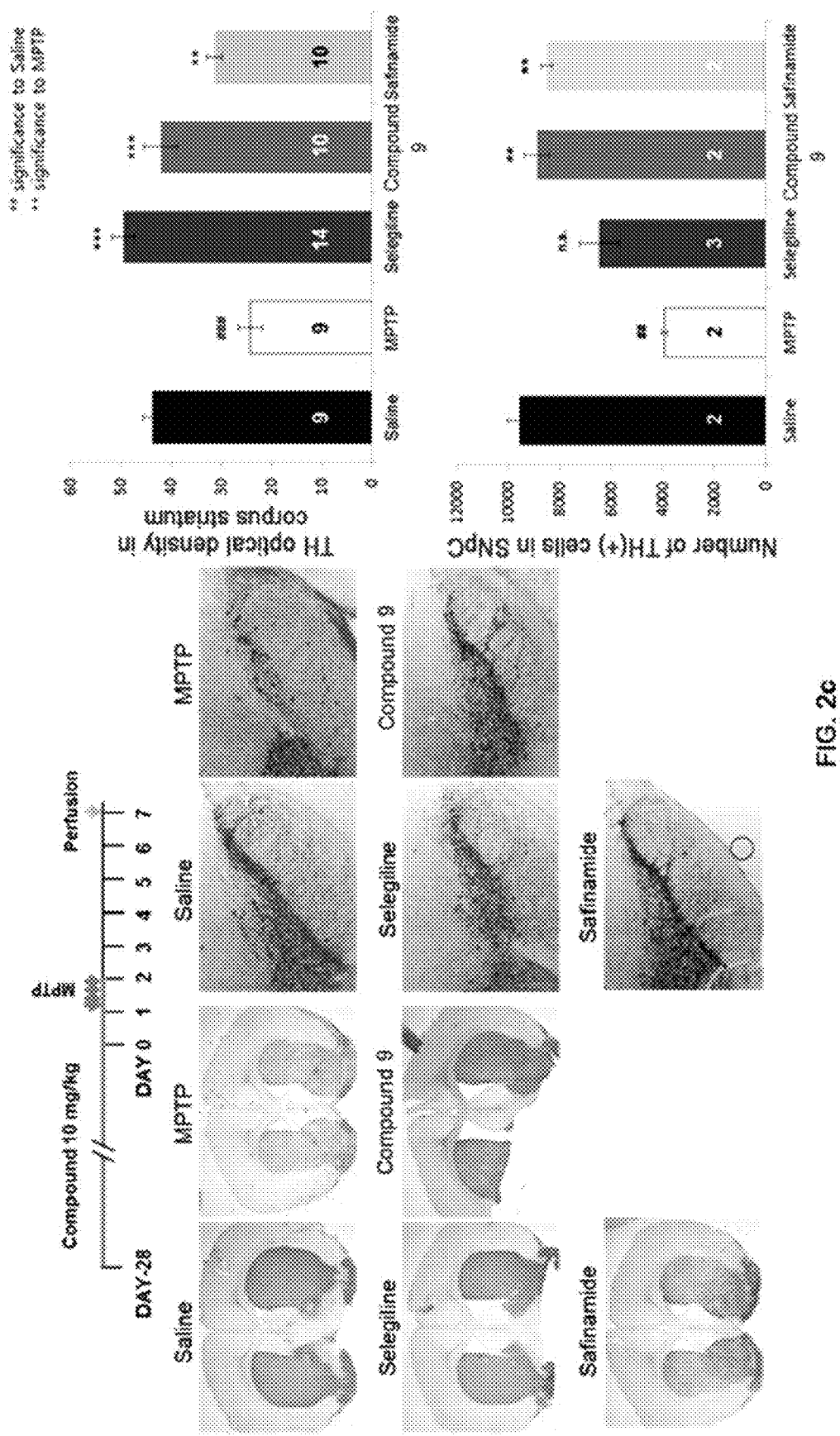
FIG. 2c shows the dopaminergic neuron protecting effect of compound 9 in the substantia nigra and the corpus striatum (30-day pre-treatment).

(3) Next, considering the long-term period of medication, it was investigated whether the administration of the MAO-B inhibitor for 30 days is effective in protecting neurons in the MPTP model of Parkinson's disease. In the corpus striatum, the irreversible inhibitors selegiline and compound 9 protected dopaminergic neurons to a level comparable to that of the control group not treated with MPTP. Safinamide exhibited slightly lower efficacy. On the other hand, in the substantia nigra, the efficacy of the irreversible inhibitor selegiline was decreased and the number of neurons did not recover significantly as compared to the MPTP group. In contrast, the reversible inhibitor compound 9 protected neurons similarly to the control group. This suggests that the MAO-B inhibitory effect of selegiline is offset upon long-term medication due to a compensatory mechanism because it inhibits MAO-B irreversibly. This is the reason why selegiline is not effective in treating Parkinson's disease upon long-term medication. That is to say, as seen from FIG. 2c, compound 9 showed superior efficacy as compared to selegiline and safinamide in the three testes on the MPTP mouse model of Parkinson's disease.

Figure 3A:
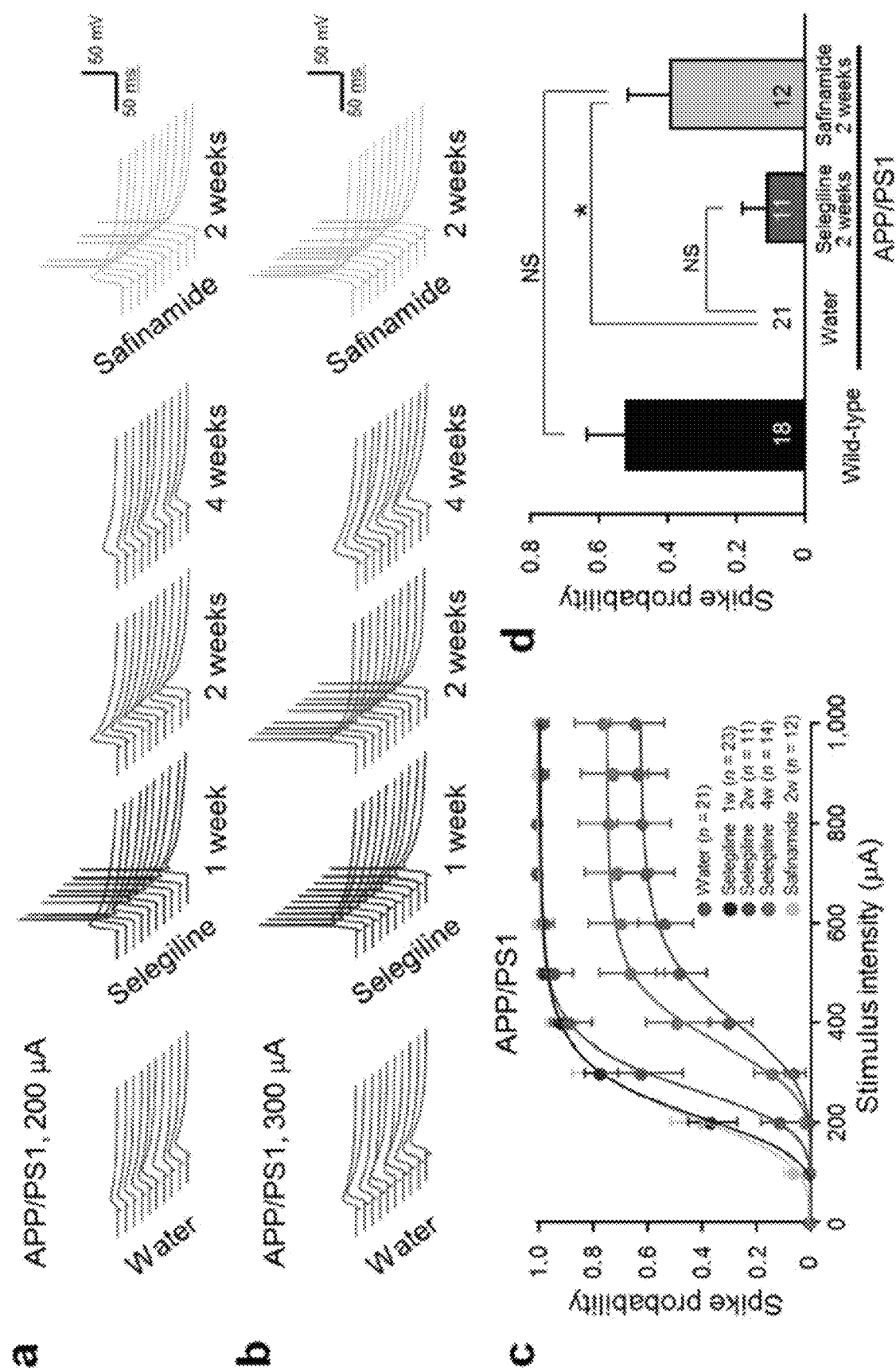
FIG. 3a shows spike probability in APP/PS1 mouse depending on stimulus intensity (Jo et al., Nature Medicine, 2014).
Figure 3B:
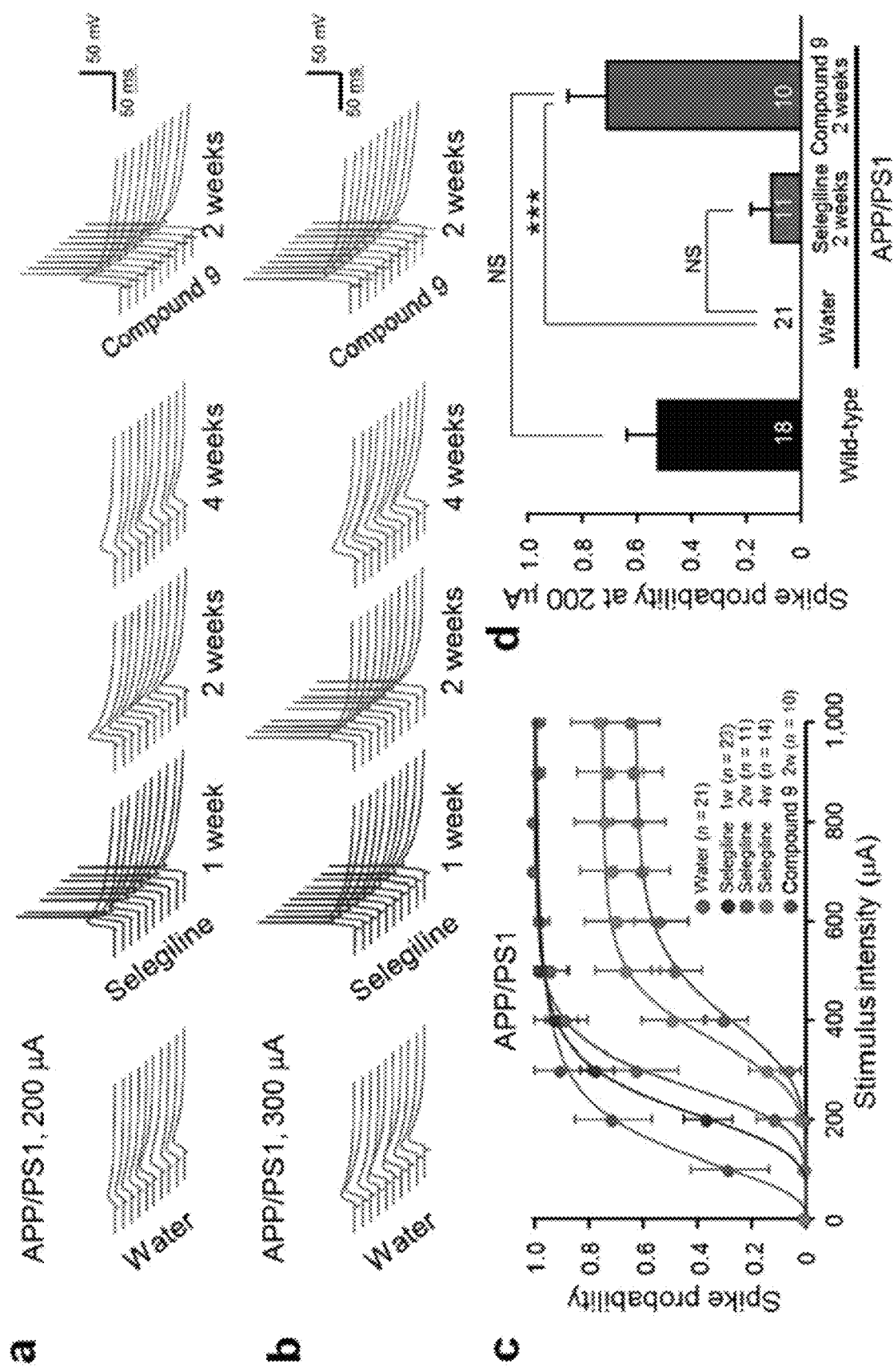
FIG. 3b shows the spike probability of compound 9 in APP/PS1 mouse depending on stimulus intensity.

Test Example 4: Efficacy of Compound 9 in APP/PS1 Mouse Model of Alzheimer's Disease The inventors of the present disclosure have recently unveiled a new possibility of Alzheimer's disease treatment through inhibition of MAO-B (Jo et al., Nature Medicine 2014). In this research, they have found out that, as shown in FIGS. 3a-3b, whereas the irreversible MAO-B inhibitor selegiline shows excellent efficacy initially in the Alzheimer's disease model but the efficacy decreases greatly after 2 weeks and no efficacy is observed after 4 weeks, the reversible MAO-B inhibitor safinamide maintains excellent efficacy even after 2 weeks.

In Test Example 4, the efficacy of the reversible MAO-B inhibitor compound 9 in APP/PS1 mouse was investigated as follows. First, APP/PS1 mouse was allowed to freely take in compound 9 for 2 weeks at a dosage of by mixing in drinking water. After 2 weeks of administration, brain tissue sections were prepared and electrodes were connected to dentate gyrus granule cells using the patch-clamp technique. The change in the membrane potential of the granule cells and spike can be detected using the electrodes. Spike probability was calculated by counting the number of spike responses of the granule cells while applying 10 electric stimulations to the dentate gyrus. When the spike probability was measured while varying the intensity of the electric stimulation after the treatment with compound 9 for 2 weeks, superior efficacy was observed as shown in FIG. 3b. The efficacy of compound 9 was higher than that of safinamide.

Test Example 5: Differentiability and Superiority of Compound 9 as Compared to Safinamide The existing reversible MAO-B inhibitor safinamide is well known not only for its MAO-B inhibitory effect but also as a sodium channel and calcium channel inhibitor. A therapeutic agent for Parkinson's disease and Alzheimer's disease which selectively inhibits MAO-B with minimized channel inhibition can have good stability as a therapeutic agent for brain disease. In order to investigate the channel inhibitory effect, inhibition of channel excitability was investigated electrophysiologically using DGGCs (dentate gyrus granule cells) of the hippocampus.

Figure 4:
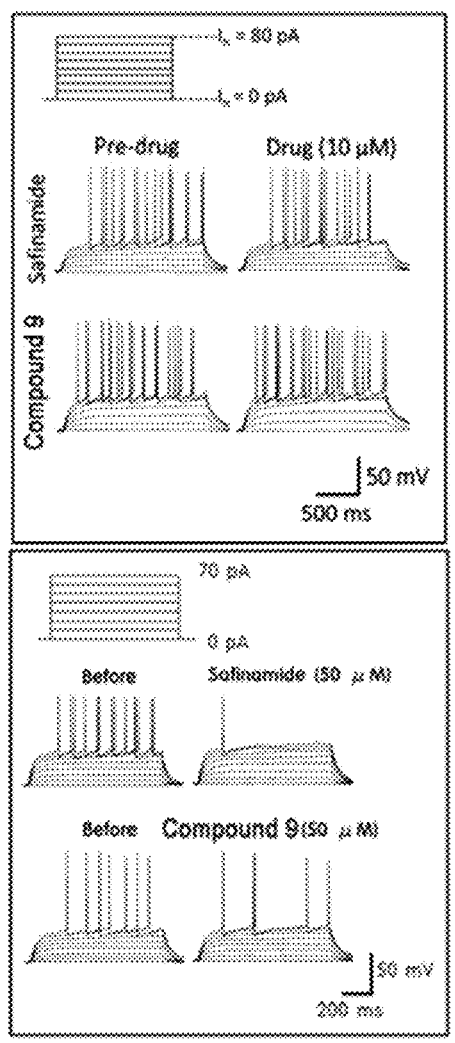
FIG. 4 shows the excitability test result of compound 9 in DGGCs (dentate gyrus granule cells).
Figure 4:
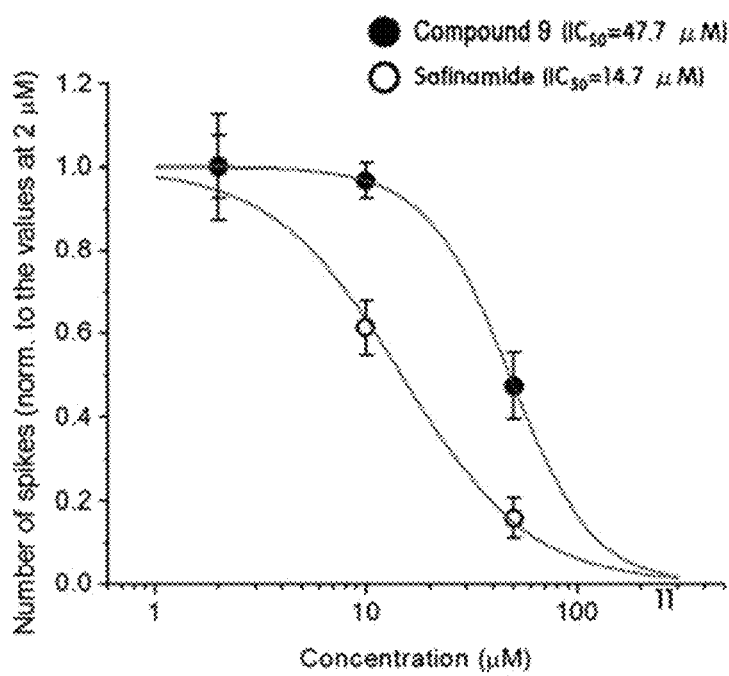

As can be seen from FIG. 4, whereas safinamide showed about 40% of excitability inhibitory effect at 10 μM, compound 9 showed almost no inhibitory effect. Compound 9 showed lower inhibitory effect than safinamide at higher concentration of 50 μM, too. This reveals that the excitability inhibitory effect of compound 9 for hippocampal DGGCs is much lower than that of safinamide. This result shows that compound 9 is stable as a selective MAO-B inhibitor due to much lower channel inhibitory effect as compared to safinamide.

Test Example 6: Molecular Modeling of Compound 9 and Safinamide for MAO-B

Figure 5:
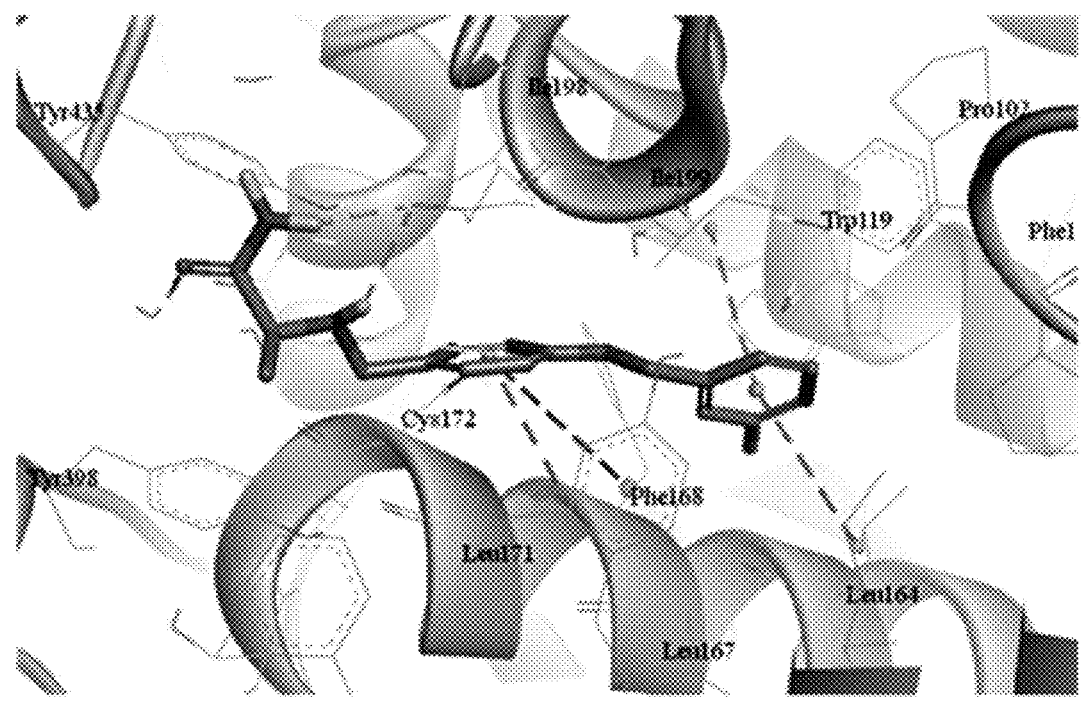
FIG. 5 shows a result of predicting the binding mode of safinamide and compound 9.
Figure 5:
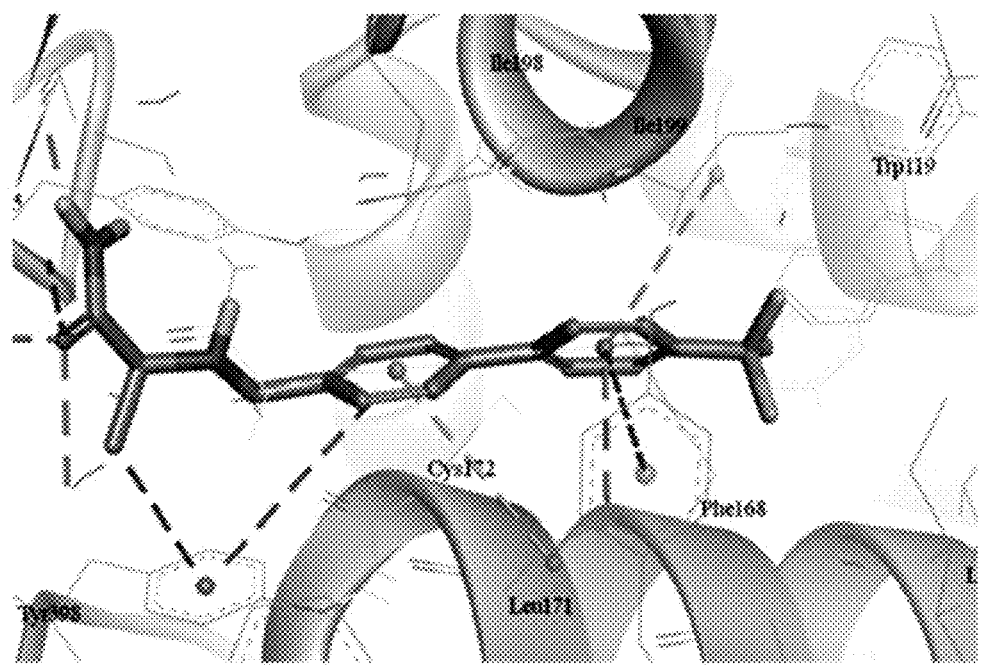

The binding mode of compound 9 for MAO-B was predicted through docking experiment. First, the binding mode of the reversible inhibitor safinamide was predicted using the MAO-B X-ray crystal structure. As shown in FIG. 5, superior binding affinity was observed at the pocket which is known as the active site of MAO-B (SP score: −10.862 kcal/mol). When calculation was conducted for compound 9, it was predicted to bind at the same active site as safinamide and the binding affinity was estimated to be stronger than safinamide (SP score: −11.795 kcal/mol).

Test Example 7: Obesity Inhibition Effect

Figure 6:
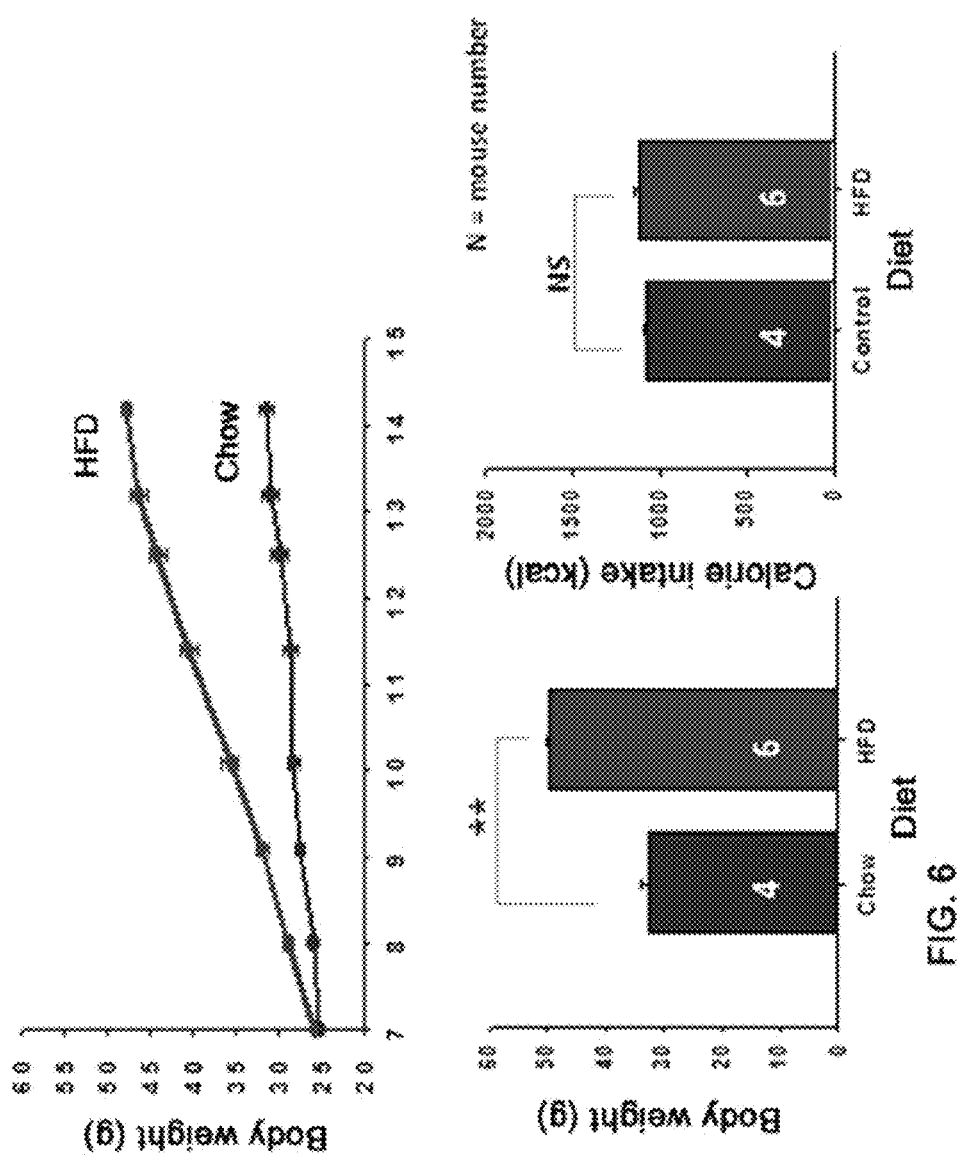
FIG. 6 shows the change in body weight of mice to which normal diet and high-fat diet were given.
Figure 6:
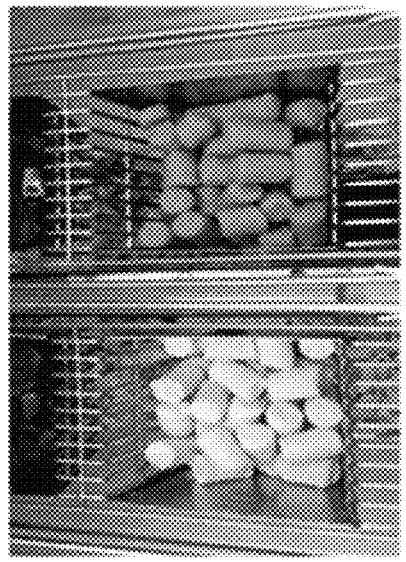
Figure 6:
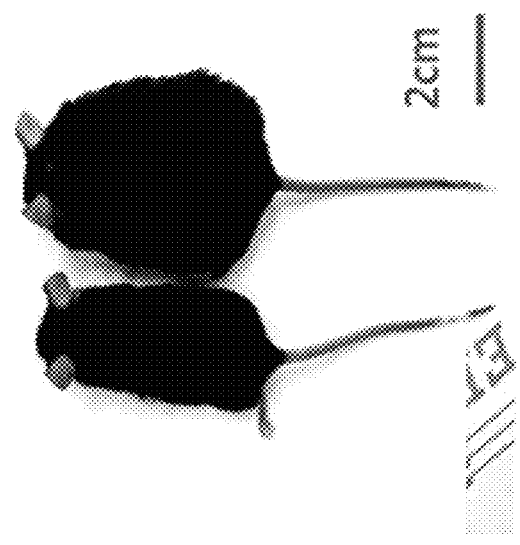

A. Establishment of Obesity Model Mouse Using High-Fat Diet 7-week-old mice were divided into 2 groups and were given a normal diet (white, chow) and a high-fat diet (blue, HFD), respectively, for 8 weeks. The result is shown in FIG. 6.

The total calorie provided to the normal diet mice and the high-fat diet mice was set to be equal. The average body weight of the normal diet group was measured to be 3 g at 8 weeks, with about 20% increase from the initial weight of 2.5 g. In contrast, the average body weight of the high-fat diet almost doubled to about 4.8 g.

B. Emergence of Reactive Astrocytes in Obesity Model Mouse

Figure 7:
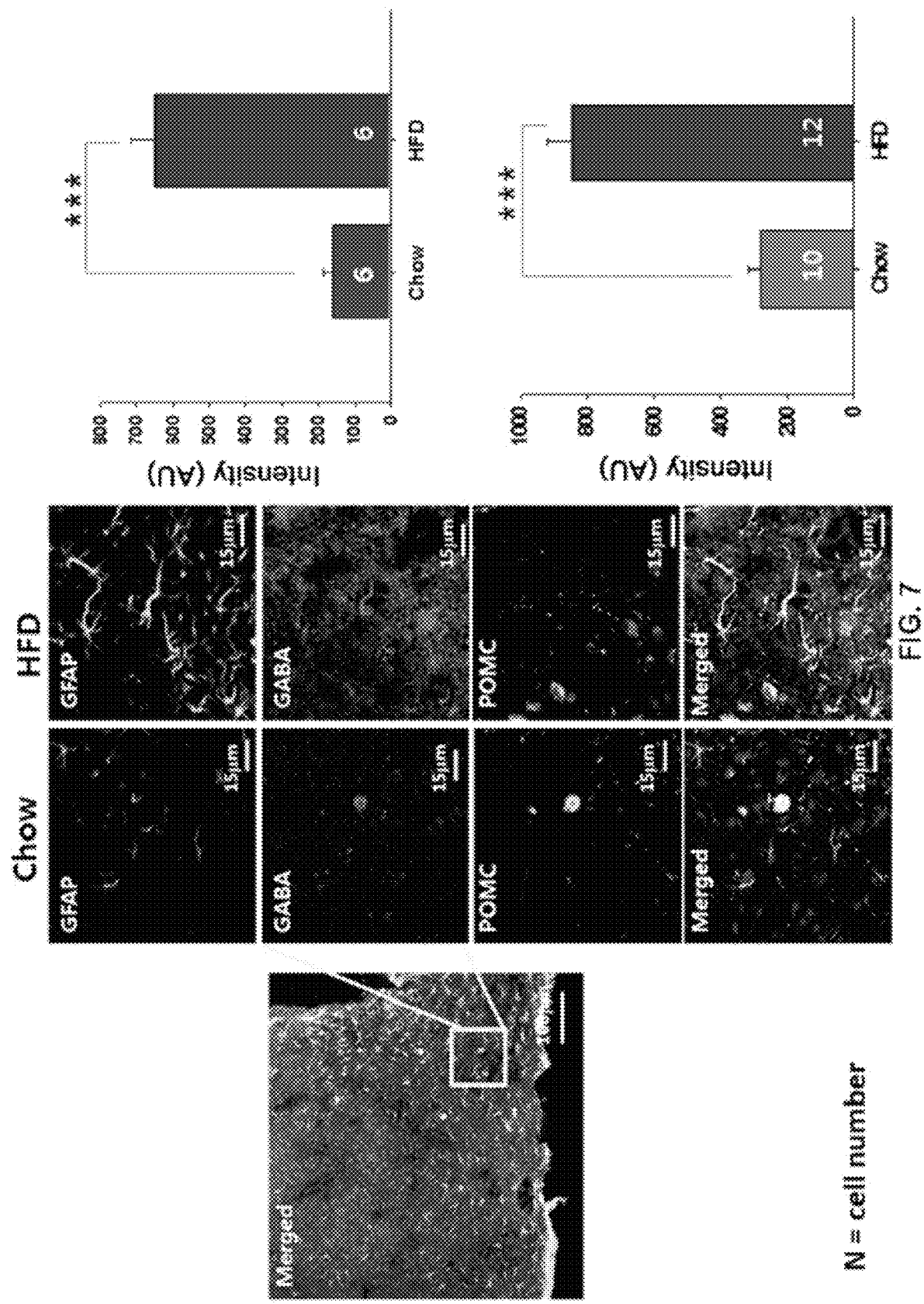
FIG. 7 shows the change in reactive astrocytes in mice to which normal diet and high-fat diet were given.

The change in reactive astrocytes was observed in the arcuate nucleus of the mice to which the high-fat diet was given for 8 weeks. As shown in FIG. 7, remarkable increase in GFAP, which is a biomarker for reactive astrocytes, was observed in the arcuate nucleus of the high-fat diet mice as compared to the normal diet mice. In addition to the increase in reactive astrocytes, overproduction of γ-aminobutyric acid (GABA) was also detected.

C. Decrease in Body Weight of Obesity Model Mouse by Compound of Example 9

Figure 8:
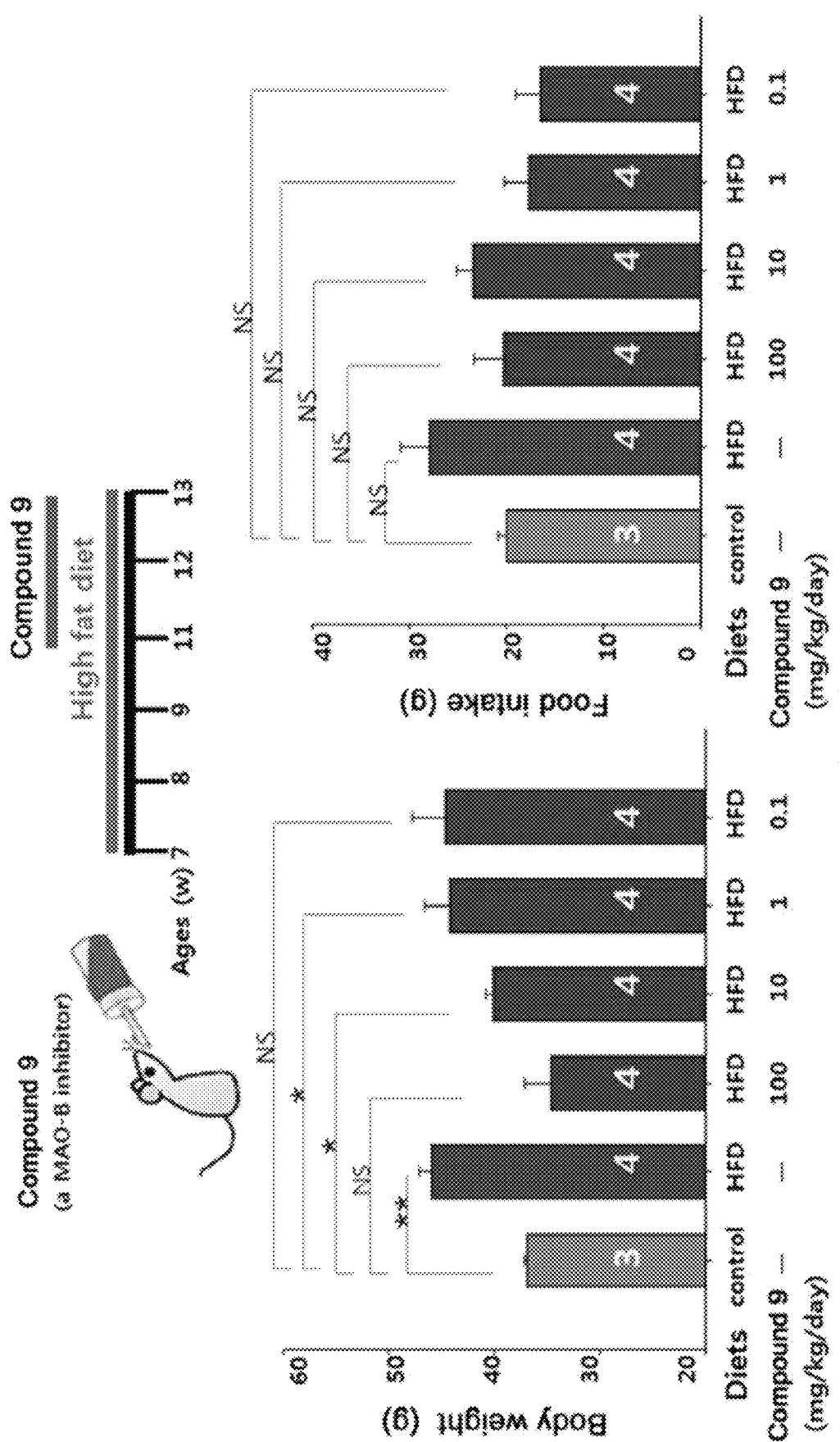
FIG. 8 shows the change in body weight of obesity model mice to which high-fat diet was given depending on the administration amount of an α-aminoamide derivative.

The body weight decreasing effect of the compound of Example 9 in the HFD (high-fat diet) mouse model of obesity was investigated. As shown in FIG. 8, the compound of Example 9 inhibited body weight increase due to the intake of the high-fat diet in a concentration-dependent manner and there was no difference in the amount of food intake. Specifically, the high-fat diet mice showed 20% or more increased body weight as compared to the normal mice (control). The administration of the compound of Example 9 resulted in decrease of the body weight. In particular, the 10 mg/kg/day group and the 100 mg/kg/day group also showed body weight decrease in a concentration-dependent manner.

D. Increase in GABA in Reactive Astrocytes of Arcuate Nucleus of Obesity Model Mouse and Decrease of GABA by Compound of Example 9

Figure 9:
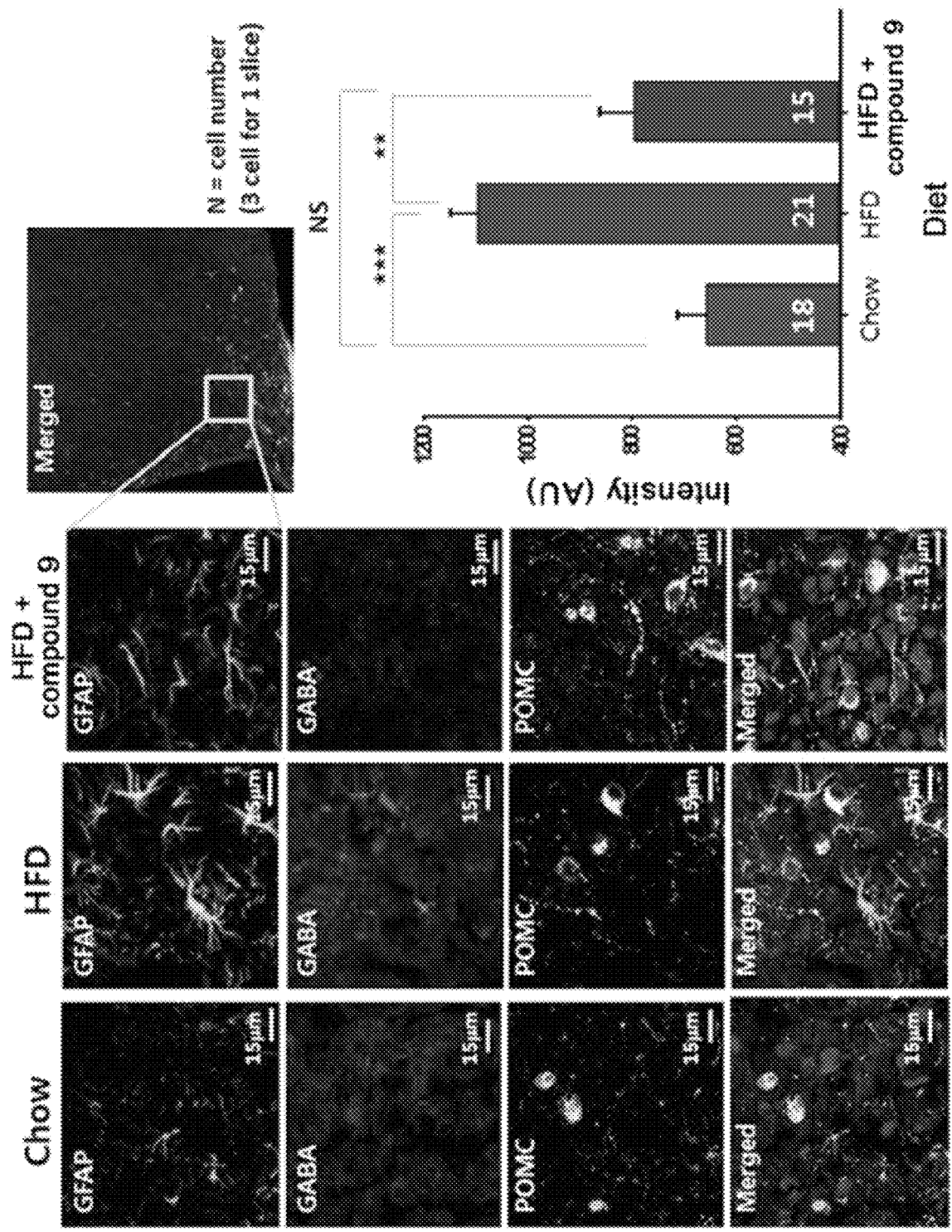
FIG. 9 shows the change in reactive astrocytes and GABA in mice to which normal diet was given, mice to which high-fat diet was given and mice to which high-fat diet was given together with an α-aminoamide derivative.

A result of administering the compound of Example 9 to the high-fat diet mice is shown in FIG. 9. Remarkable decrease in GFAP, which is a biomarker for reactive astrocytes, was observed in the arcuate nucleus and effective inhibition of the overproduction of GABA was also confirmed.

Through these results, it can be seen that a composition containing the α-aminoamide derivative according to the present disclosure as an active ingredient can be usefully used as a therapeutic agent for obesity because the α-aminoamide derivative can exhibit anti-obesity efficacy by reversibly inhibiting MAO-B.

INDUSTRIAL APPLICABILITY

Because the α-aminoamide derivative can prevent overproduction of GABA in reactive astrocytes of the hypothalamus by inhibiting MAO-B, it can exhibit an effect of treating obesity by acting on POMC neurons which selectively induce energy consumption. Accordingly, it can overcome the side effect and efficacy problems of the existing obesity therapeutic agents centered on the central nervous system and regulation of sugar/fat metabolism and can be usefully used as a new obesity therapeutic agent. In addition, it can be usefully used as a therapeutic agent for a neurodegenerative disease such as Parkinson's disease, Alzheimer's disease, etc. because it can inhibit the denaturation or destruction of dopaminergic neurons.

The invention claimed is:
1. A pharmaceutical composition for treating a neurodegenerative disease, which comprises the α-aminoamide derivative according to Chemical Formula 1 or a pharmaceutically acceptable salt thereof as an active ingredient,

Chemical Formula 1

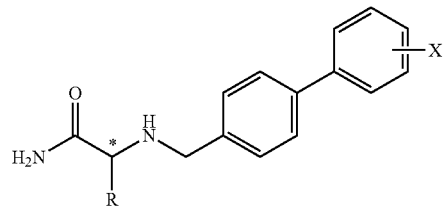

wherein
R is hydrogen or $C_{1-7}$ alkyl; and
X is selected from the group consisting of a halogen, alkyl, halogenated alkyl, alkoxy and halogenated alkoxy.
2. The pharmaceutical composition for treating a neurodegenerative disease according to claim 1, wherein the neurodegenerative disease is selected from Parkinson's disease, Alzheimer's disease, epilepsy and depression.

* * * * *